US006465632B1

(12) United States Patent
Walke et al.

(10) Patent No.: US 6,465,632 B1

(45) Date of Patent: Oct. 15, 2002

(54) HUMAN PHOSPHATASES AND POLYNUCLEOTIDES ENCODING THE SAME

(75) Inventors: D. Wade Walke, Spring; John Scoville, Houston; C. Alexander Turner, Jr., The Woodlands; Glenn Friedrich, Houston; Alejandro Abuin, The Woodlands; Brian Zambrowicz, The Woodlands; Arthur T. Sands, The Woodlands, all of TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/877,730

(22) Filed: Jun. 8, 2001

Related U.S. Application Data

(60) Provisional application No. 60/210,607, filed on Jun. 9, 2000.

(51) Int. Cl.[7] .......................... C07H 21/04; C12N 9/12

(52) U.S. Cl. .................. 536/23.2; 536/23.1; 536/23.5; 435/183; 435/194

(58) Field of Search ................................ 435/183, 194; 536/23.1, 23.2; 530/350

(56) References Cited

U.S. PATENT DOCUMENTS

| | | | | |
|---|---|---|---|---|
| 4,215,051 | A | 7/1980 | Schroeder et al. | 260/346.7 |
| 4,376,110 | A | 3/1983 | David et al. | 436/513 |
| 4,946,778 | A | 8/1990 | Ladner et al. | 435/69.6 |
| 5,723,323 | A | 3/1998 | Kauffman et al. | 435/172.3 |
| 5,830,721 | A | 11/1998 | Stemmer et al. | 435/172.1 |
| 5,837,458 | A | 11/1998 | Minshull et al. | 435/6 |
| 5,869,336 | A | 2/1999 | Meyer et al. | 435/348 |
| 5,939,271 | A | 8/1999 | Tessier-Lavigne et al. | 435/7.1 |
| 6,020,179 | A | 2/2000 | Goli | 435/196 |

OTHER PUBLICATIONS

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Repertoire in Phage Lambda", Science 246:1275–1281.

Huston et al, 1988, "Protein engeineering of antibody binding sites: Recovery of specific activity in an anti–diogoxin single–chain Fv analogue produced in *Escherichia coil*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the Ipp gene of Escherichia coil", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli*gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10): 1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

(List continued on next page.)

*Primary Examiner*—Rebecca E. Prouty

(57) ABSTRACT

Novel human polynucleotide and polypeptide sequences are disclosed that can be used in therapeutic, diagnostic, and pharmacogenomic applications.

2 Claims, No Drawings

OTHER PUBLICATIONS

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coil*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

SEQUENCE LISTING

```
<160> NUMBER OF SEQ ID NOS: 31

<210> SEQ ID NO 1
<211> LENGTH: 3210
<212> TYPE: DNA
<213> ORGANISM: homo sapiens

<400> SEQUENCE: 1

atggcgcctc ctctgcgacc cctcgcccgg ctgcgaccgc cggggatgct gctccgcgcg      60

ctcctgctcc tgctgmtgct cagtcctttg ccaggagtgt ggtgctttag cgaactgtct     120

tttgtaaaag aaccacagga tgtaactgtc acaagaaagg acccagtcgt tttagattgc     180

caggctcacg gagaagttcc tattaaggtc acatggttga aaaatggagc aaaaatgtct     240

gaaaataaac ggatcgaggt tctttctaac ggctctttat acatcagtga ggtggaaggc     300

aggcgaggag agcagtccga tgaaggattt tatcagtgct tggcaatgaa caaatatgga     360

gccattctta gtcaaaaagc tcatcttgcc ttatcaacta tttctgcatt tgaagtccag     420

ccaatttcca ctgaggtcca cgaaggtgga gttgctcgat ttgcatgcaa gatttcatcc     480

caccctcctg cagtcataac atgggagttc aatcggacaa ctctacctat gactatggac     540

aggataactg ccctaccaac aggagtattg cagatctatg atgtcagcca aagggattct     600

ggaaattatc gttgtattgc tgccactgta gcccaccgac gtaaaagtat ggaggcctcg     660

ctaactgtga ttccagctaa ggagtcaaaa tccttccaca caccarcaat tatagcaggt     720

ccacagaaca taacaacatc tcttcatcag actgtagttt tggaatgcat ggccacagga     780
```

-continued

```
aatcccaaac caatcatttc ttggagccgc cttgatcaca aatccattga tgtctttaat    840
actcgggtac ttggaaatgg taatctcatg atatctgatg tcaggctaca acatgctgga    900
gtatatgttt gtcgggccac taccccctggc acacgcaact ttacagttgc tatggcaact    960
ttaactgtat tagctcctcc ttcatttgtt gaatggccag aaagtttaac aaggcctcga   1020
gctggcactg ctcgatttgt gtgtcaggca gaaggaatcc cctctcccaa gatgtcatgg   1080
ttgaaaaatg gaaggaagat acattcgaat ggtagaatta aaatgtacaa cagtaaattg   1140
gtaattaacc agattattcc tgaagatgat gctatttatc agtgcatggc tgagaatagc   1200
caaggatcta ttttatctag agccagactg actgtagtga tgtcagaaga cagacccagt   1260
gctccctata atgtacatgc tgaaaccatg tcaagctcag ccattctttt agcctgggag   1320
aggccacttt ataattcaga caaagtcatt gcctattctg tacactacat gaaagcagaa   1380
ggtttaaata atgaagagta tcaagtagtc atcggaaatg acacaactca ttatattatt   1440
gatgacttag agcctgccag caattatact ttctacattg tagcatatat gccaatggga   1500
gccagccaga tgtctgacca tgtgacacag aatactctag aggatgttcc cctgagacct   1560
cctgaaatta gtttgacaag tcgaagtccc actgatattc tcatctcctg gctgccaatc   1620
ccagccaaat atcggcgggg ccaagtggtg ctgtatcgct tgtctttccg cctaagtact   1680
gagaattcaa tccaagttct ggagctcccg ggaccacgc atgagtacct tttggaaggc   1740
ctgaaacctg acagtgtcta cctggttcgg attactgctg ccaccagagt ggggctggga   1800
gagtcatcag tatggacttc acataggacg cccaaagcta caagcgtgaa agcccctaag   1860
tctccagagt tgcatttgga gcctctgaac tgtaccacca tttctgtgag gtggcagcaa   1920
gatgtagagg acacagctgc tattcagggc tacaagctgt actacaagga agaagggcag   1980
caggagaatg ggcccatttt cttggatacc aaggacctac tctatactct cagtggctta   2040
gaccccagaa gaaaatatca tgtgagactc ctggcttaca acaacataga cgatggctat   2100
caggcagatc agactgtcag cactccagga tgcgtgtctg ttcgtgatcg catggtccct   2160
cctccaccac caccccacca tctctatgcg aaggctaaca cctcatcttc catcttcctg   2220
cactggagga ggcctgcatt caccgctgca caaatcatta actacaccat ccgctgtaat   2280
cctgttggcc tgcagaatgc ttctttggtt ctgtaccttc aaacatcaga aactcacatg   2340
ttggttcaag gtctagaacc aaacaccaaa tacgaatttg ccgttcgatt acatgtggat   2400
cagctttcca gtccttggag ccctgtagtc taccattcta ctcttccaga agcaccagca   2460
ggcccaccag ttggagtaaa agtgacatta atagaggatg acactgccct ggtttcttgg   2520
aaacccccctg atggcccaga aacagttgtg acccgctata ctatcttata tgcatctagg   2580
aaggcctgga ttgcaggaga gtggcaggtc ttacaccgtg aaggggcaat aaccatggct   2640
ttgctagaaa acttggtagc aggaaatgtg tacattgtca agatatctgc atccaatgag   2700
gtgggagaag gacccttttc aaattctgtg gagctggcag tacttccaaa ggaaacctct   2760
gaatcaaatc agaggcccaa gcgtttagat tctgctgatg ccaaagttta ttcaggatat   2820
taccatctgg accaaaaatc aatgactggc attgctgtag gtgttggcat agccttgacc   2880
tgcatcctca tctgtgttct catcttgata taccgaagta aagccaggaa atcatctgct   2940
tccaagacgg cacagaatgg aactcaacag ttacctcgta ccagtgcctc cttagctagt   3000
ggaaatgagg taggaaagaa cctggaagga gctgtaggaa atgaagaatc tttaatgcca   3060
atgatcatgc caaacagctt cattgatgca aaggtactga gctgcgggat ttgctgcata   3120
```

-continued

```
agccgttctt ccattcctcc tccctgtgtg tgtaaaatgt acttcccccca aaattgtatg   3180

ttgaatgtat tataccaata ctcttattaa                                      3210


<210> SEQ ID NO 2
<211> LENGTH: 1069
<212> TYPE: PRT
<213> ORGANISM: homo sapiens

<400> SEQUENCE: 2

Met Ala Pro Pro Leu Arg Pro Leu Ala Arg Leu Arg Pro Pro Gly Met
 1               5                  10                  15

Leu Leu Arg Ala Leu Leu Leu Leu Leu Leu Leu Ser Pro Leu Pro Gly
            20                  25                  30

Val Trp Cys Phe Ser Glu Leu Ser Phe Val Lys Glu Pro Gln Asp Val
        35                  40                  45

Thr Val Thr Arg Lys Asp Pro Val Val Leu Asp Cys Gln Ala His Gly
    50                  55                  60

Glu Val Pro Ile Lys Val Thr Trp Leu Lys Asn Gly Ala Lys Met Ser
65                  70                  75                  80

Glu Asn Lys Arg Ile Glu Val Leu Ser Asn Gly Ser Leu Tyr Ile Ser
                85                  90                  95

Glu Val Glu Gly Arg Arg Gly Glu Gln Ser Asp Glu Gly Phe Tyr Gln
            100                 105                 110

Cys Leu Ala Met Asn Lys Tyr Gly Ala Ile Leu Ser Gln Lys Ala His
        115                 120                 125

Leu Ala Leu Ser Thr Ile Ser Ala Phe Glu Val Gln Pro Ile Ser Thr
    130                 135                 140

Glu Val His Glu Gly Gly Val Ala Arg Phe Ala Cys Lys Ile Ser Ser
145                 150                 155                 160

His Pro Pro Ala Val Ile Thr Trp Glu Phe Asn Arg Thr Thr Leu Pro
                165                 170                 175

Met Thr Met Asp Arg Ile Thr Ala Leu Pro Thr Gly Val Leu Gln Ile
            180                 185                 190

Tyr Asp Val Ser Gln Arg Asp Ser Gly Asn Tyr Arg Cys Ile Ala Ala
        195                 200                 205

Thr Val Ala His Arg Arg Lys Ser Met Glu Ala Ser Leu Thr Val Ile
    210                 215                 220

Pro Ala Lys Glu Ser Lys Ser Phe His Thr Pro Thr Ile Ile Ala Gly
225                 230                 235                 240

Pro Gln Asn Ile Thr Thr Ser Leu His Gln Thr Val Val Leu Glu Cys
                245                 250                 255

Met Ala Thr Gly Asn Pro Lys Pro Ile Ile Ser Trp Ser Arg Leu Asp
            260                 265                 270

His Lys Ser Ile Asp Val Phe Asn Thr Arg Val Leu Gly Asn Gly Asn
        275                 280                 285

Leu Met Ile Ser Asp Val Arg Leu Gln His Ala Gly Val Tyr Val Cys
    290                 295                 300

Arg Ala Thr Thr Pro Gly Thr Arg Asn Phe Thr Val Ala Met Ala Thr
305                 310                 315                 320

Leu Thr Val Leu Ala Pro Pro Ser Phe Val Glu Trp Pro Glu Ser Leu
                325                 330                 335

Thr Arg Pro Arg Ala Gly Thr Ala Arg Phe Val Cys Gln Ala Glu Gly
            340                 345                 350

Ile Pro Ser Pro Lys Met Ser Trp Leu Lys Asn Gly Arg Lys Ile His
```

-continued

```
        355                 360                 365

Ser Asn Gly Arg Ile Lys Met Tyr Asn Ser Lys Leu Val Ile Asn Gln
    370                 375                 380

Ile Ile Pro Glu Asp Asp Ala Ile Tyr Gln Cys Met Ala Glu Asn Ser
385                 390                 395                 400

Gln Gly Ser Ile Leu Ser Arg Ala Arg Leu Thr Val Val Met Ser Glu
                405                 410                 415

Asp Arg Pro Ser Ala Pro Tyr Asn Val His Ala Glu Thr Met Ser Ser
            420                 425                 430

Ser Ala Ile Leu Leu Ala Trp Glu Arg Pro Leu Tyr Asn Ser Asp Lys
        435                 440                 445

Val Ile Ala Tyr Ser Val His Tyr Met Lys Ala Glu Gly Leu Asn Asn
    450                 455                 460

Glu Glu Tyr Gln Val Val Ile Gly Asn Asp Thr Thr His Tyr Ile Ile
465                 470                 475                 480

Asp Asp Leu Glu Pro Ala Ser Asn Tyr Thr Phe Tyr Ile Val Ala Tyr
                485                 490                 495

Met Pro Met Gly Ala Ser Gln Met Ser Asp His Val Thr Gln Asn Thr
            500                 505                 510

Leu Glu Asp Val Pro Leu Arg Pro Pro Glu Ile Ser Leu Thr Ser Arg
        515                 520                 525

Ser Pro Thr Asp Ile Leu Ile Ser Trp Leu Pro Ile Pro Ala Lys Tyr
    530                 535                 540

Arg Arg Gly Gln Val Val Leu Tyr Arg Leu Ser Phe Arg Leu Ser Thr
545                 550                 555                 560

Glu Asn Ser Ile Gln Val Leu Glu Leu Pro Gly Thr Thr His Glu Tyr
                565                 570                 575

Leu Leu Glu Gly Leu Lys Pro Asp Ser Val Tyr Leu Val Arg Ile Thr
            580                 585                 590

Ala Ala Thr Arg Val Gly Leu Gly Glu Ser Ser Val Trp Thr Ser His
        595                 600                 605

Arg Thr Pro Lys Ala Thr Ser Val Lys Ala Pro Lys Ser Pro Glu Leu
    610                 615                 620

His Leu Glu Pro Leu Asn Cys Thr Thr Ile Ser Val Arg Trp Gln Gln
625                 630                 635                 640

Asp Val Glu Asp Thr Ala Ala Ile Gln Gly Tyr Lys Leu Tyr Tyr Lys
                645                 650                 655

Glu Glu Gly Gln Gln Glu Asn Gly Pro Ile Phe Leu Asp Thr Lys Asp
            660                 665                 670

Leu Leu Tyr Thr Leu Ser Gly Leu Asp Pro Arg Arg Lys Tyr His Val
        675                 680                 685

Arg Leu Leu Ala Tyr Asn Asn Ile Asp Asp Gly Tyr Gln Ala Asp Gln
    690                 695                 700

Thr Val Ser Thr Pro Gly Cys Val Ser Val Arg Asp Arg Met Val Pro
705                 710                 715                 720

Pro Pro Pro Pro Pro His His Leu Tyr Ala Lys Ala Asn Thr Ser Ser
                725                 730                 735

Ser Ile Phe Leu His Trp Arg Arg Pro Ala Phe Thr Ala Ala Gln Ile
            740                 745                 750

Ile Asn Tyr Thr Ile Arg Cys Asn Pro Val Gly Leu Gln Asn Ala Ser
        755                 760                 765

Leu Val Leu Tyr Leu Gln Thr Ser Glu Thr His Met Leu Val Gln Gly
    770                 775                 780
```

-continued

```
Leu Glu Pro Asn Thr Lys Tyr Glu Phe Ala Val Arg Leu His Val Asp
785                 790                 795                 800

Gln Leu Ser Ser Pro Trp Ser Pro Val Val Tyr His Ser Thr Leu Pro
                805                 810                 815

Glu Ala Pro Ala Gly Pro Pro Val Gly Val Lys Val Thr Leu Ile Glu
            820                 825                 830

Asp Asp Thr Ala Leu Val Ser Trp Lys Pro Pro Asp Gly Pro Glu Thr
        835                 840                 845

Val Val Thr Arg Tyr Thr Ile Leu Tyr Ala Ser Arg Lys Ala Trp Ile
    850                 855                 860

Ala Gly Glu Trp Gln Val Leu His Arg Glu Gly Ala Ile Thr Met Ala
865                 870                 875                 880

Leu Leu Glu Asn Leu Val Ala Gly Asn Val Tyr Ile Val Lys Ile Ser
                885                 890                 895

Ala Ser Asn Glu Val Gly Glu Gly Pro Phe Ser Asn Ser Val Glu Leu
            900                 905                 910

Ala Val Leu Pro Lys Glu Thr Ser Glu Ser Asn Gln Arg Pro Lys Arg
        915                 920                 925

Leu Asp Ser Ala Asp Ala Lys Val Tyr Ser Gly Tyr Tyr His Leu Asp
    930                 935                 940

Gln Lys Ser Met Thr Gly Ile Ala Val Gly Val Gly Ile Ala Leu Thr
945                 950                 955                 960

Cys Ile Leu Ile Cys Val Leu Ile Leu Ile Tyr Arg Ser Lys Ala Arg
                965                 970                 975

Lys Ser Ser Ala Ser Lys Thr Ala Gln Asn Gly Thr Gln Gln Leu Pro
            980                 985                 990

Arg Thr Ser Ala Ser Leu Ala Ser Gly Asn Glu Val Gly Lys Asn Leu
        995                 1000                1005

Glu Gly Ala Val Gly Asn Glu Glu Ser Leu Met Pro Met Ile Met Pro
    1010                1015                1020

Asn Ser Phe Ile Asp Ala Lys Val Leu Ser Cys Gly Ile Cys Cys Ile
1025                1030                1035                1040

Ser Arg Ser Ser Ile Pro Pro Pro Cys Val Cys Lys Met Tyr Phe Pro
                1045                1050                1055

Gln Asn Cys Met Leu Asn Val Leu Tyr Gln Tyr Ser Tyr
            1060                1065
```

```
<210> SEQ ID NO 3
<211> LENGTH: 1143
<212> TYPE: DNA
<213> ORGANISM: homo sapiens

<400> SEQUENCE: 3

atggcgcctc ctctgcgacc cctcgcccgg ctgcgaccgc cggggatgct gctccgcgcg      60

ctcctgctcc tgctgmtgct cagtcctttg ccaggagtgt ggtgctttag cgaactgtct     120

tttgtaaaag aaccacagga tgtaactgtc acaagaaagg acccagtcgt tttagattgc     180

caggctcacg gagaagttcc tattaaggtc acatggttga aaaatggagc aaaaatgtct     240

gaaaataaac ggatcgaggt tctttctaac ggctctttat acatcagtga ggtggaaggc     300

aggcgaggag agcagtccga tgaaggattt tatcagtgct tggcaatgaa caaatatgga     360

gccattctta gtcaaaaagc tcatcttgcc ttatcaacta tttctgcatt tgaagtccag     420

ccaatttcca ctgaggtcca cgaaggtgga gttgctcgat ttgcatgcaa gatttcatcc     480
```

-continued

```
caccctcctg cagtcataac atgggagttc aatcggacaa ctctacctat gactatggac    540

aggataactg ccctaccaac aggagtattg cagatctatg atgtcagcca aagggattct    600

ggaaattatc gttgtattgc tgccactgta gcccaccgac gtaaaagtat ggaggcctcg    660

ctaactgtga ttccagctaa ggagtcaaaa tccttccaca caccarcaat tatagcaggt    720

ccacagaaca taacaacatc tcttcatcag actgtagttt tggaatgcat ggccacagga    780

aatcccaaac caatcatttc ttggagccgc cttgatcaca aatccattga tgtctttaat    840

actcgggtac ttggaaatgg taatctcatg atatctgatg tcaggctaca acatgctgga    900

gtatatgttt gtcgggccac taccccctggc acacgcaact ttacagttgc tatggcaact    960

ttaactgtat tagctcctcc ttcatttgtt gaatggccag aaagtttaac aaggcctcga   1020

gctggcactg ctcgatttgt gtgtcaggca gaaggaatcc cctctcccaa gatgtcatgg   1080

ttgaaaaatg gaaggaagat acattcgaat ggtagaatta aaatgtacaa caggtttaaa   1140

taa                                                                 1143


<210> SEQ ID NO 4
<211> LENGTH: 380
<212> TYPE: PRT
<213> ORGANISM: homo sapiens

<400> SEQUENCE: 4

Met Ala Pro Pro Leu Arg Pro Leu Ala Arg Leu Arg Pro Pro Gly Met
 1               5                  10                  15

Leu Leu Arg Ala Leu Leu Leu Leu Leu Leu Leu Ser Pro Leu Pro Gly
            20                  25                  30

Val Trp Cys Phe Ser Glu Leu Ser Phe Val Lys Glu Pro Gln Asp Val
        35                  40                  45

Thr Val Thr Arg Lys Asp Pro Val Val Leu Asp Cys Gln Ala His Gly
    50                  55                  60

Glu Val Pro Ile Lys Val Thr Trp Leu Lys Asn Gly Ala Lys Met Ser
65                  70                  75                  80

Glu Asn Lys Arg Ile Glu Val Leu Ser Asn Gly Ser Leu Tyr Ile Ser
                85                  90                  95

Glu Val Glu Gly Arg Arg Gly Glu Gln Ser Asp Glu Gly Phe Tyr Gln
            100                 105                 110

Cys Leu Ala Met Asn Lys Tyr Gly Ala Ile Leu Ser Gln Lys Ala His
        115                 120                 125

Leu Ala Leu Ser Thr Ile Ser Ala Phe Glu Val Gln Pro Ile Ser Thr
    130                 135                 140

Glu Val His Glu Gly Gly Val Ala Arg Phe Ala Cys Lys Ile Ser Ser
145                 150                 155                 160

His Pro Pro Ala Val Ile Thr Trp Glu Phe Asn Arg Thr Thr Leu Pro
                165                 170                 175

Met Thr Met Asp Arg Ile Thr Ala Leu Pro Thr Gly Val Leu Gln Ile
            180                 185                 190

Tyr Asp Val Ser Gln Arg Asp Ser Gly Asn Tyr Arg Cys Ile Ala Ala
        195                 200                 205

Thr Val Ala His Arg Arg Lys Ser Met Glu Ala Ser Leu Thr Val Ile
    210                 215                 220

Pro Ala Lys Glu Ser Lys Ser Phe His Thr Pro Thr Ile Ile Ala Gly
225                 230                 235                 240

Pro Gln Asn Ile Thr Thr Ser Leu His Gln Thr Val Val Leu Glu Cys
                245                 250                 255
```

```
Met Ala Thr Gly Asn Pro Lys Pro Ile Ile Ser Trp Ser Arg Leu Asp
            260                 265                 270

His Lys Ser Ile Asp Val Phe Asn Thr Arg Val Leu Gly Asn Gly Asn
        275                 280                 285

Leu Met Ile Ser Asp Val Arg Leu Gln His Ala Gly Val Tyr Val Cys
    290                 295                 300

Arg Ala Thr Thr Pro Gly Thr Arg Asn Phe Thr Val Ala Met Ala Thr
305                 310                 315                 320

Leu Thr Val Leu Ala Pro Pro Ser Phe Val Glu Trp Pro Glu Ser Leu
                325                 330                 335

Thr Arg Pro Arg Ala Gly Thr Ala Arg Phe Val Cys Gln Ala Glu Gly
            340                 345                 350

Ile Pro Ser Pro Lys Met Ser Trp Leu Lys Asn Gly Arg Lys Ile His
        355                 360                 365

Ser Asn Gly Arg Ile Lys Met Tyr Asn Arg Phe Lys
    370                 375                 380


<210> SEQ ID NO 5
<211> LENGTH: 2715
<212> TYPE: DNA
<213> ORGANISM: homo sapiens

<400> SEQUENCE: 5

atggcgcctc ctctgcgacc cctcgcccgg ctgcgaccgc cggggatgct gctccgcgcg     60

ctcctgctcc tgctgmtgct cagtcctttg ccaggagtgt ggtgctttag cgaactgtct    120

tttgtaaaag aaccacagga tgtaactgtc acaagaaagg acccagtcgt tttagattgc    180

caggctcacg gagaagttcc tattaaggtc acatggttga aaaatggagc aaaaatgtct    240

gaaaataaac ggatcgaggt tctttctaac ggctctttat acatcagtga ggtggaaggc    300

aggcgaggag agcagtccga tgaaggattt tatcagtgct tggcaatgaa caaatatgga    360

gccattctta gtcaaaaagc tcatcttgcc ttatcaacta tttctgcatt tgaagtccag    420

ccaatttcca ctgaggtcca cgaaggtgga gttgctcgat ttgcatgcaa gatttcatcc    480

caccctcctg cagtcataac atgggagttc aatcggacaa ctctacctat gactatggac    540

aggataactg ccctaccaac aggagtattg cagatctatg atgtcagcca aagggattct    600

ggaaattatc gttgtattgc tgccactgta gcccaccgac gtaaaagtat ggaggcctcg    660

ctaactgtga ttccagctaa ggagtcaaaa tccttccaca caccarcaat tatagcaggt    720

ccacagaaca taacaacatc tcttcatcag actgtagttt tggaatgcat ggccacagga    780

aatcccaaac caatcatttc ttggagccgc cttgatcaca aatccattga tgtctttaat    840

actcgggtac ttggaaatgg taatctcatg atatctgatg tcaggctaca acatgctgga    900

gtatatgttt gtcgggccac taccccctggc acacgcaact ttacagttgc tatggcaact    960

ttaactgtat tagctcctcc ttcatttgtt gaatggccag aaagtttaac aaggcctcga   1020

gctggcactg ctcgatttgt gtgtcaggca gaaggaatcc cctctcccaa gatgtcatgg   1080

ttgaaaaatg gaaggaagat acattcgaat ggtagaatta aaatgtacaa cagtaaattg   1140

gtaattaacc agattattcc tgaagatgat gctatttatc agtgcatggc tgagaatagc   1200

caaggatcta ttttatctag agccagactg actgtagtga tgtcagaaga cagacccagt   1260

gctccctata atgtacatgc tgaaaccatg tcaagctcag ccattctttt agcctgggag   1320

aggccacttt ataattcaga caaagtcatt gcctattctg tacactacat gaaagcagaa   1380
```

-continued

```
ggtttaaata atgaagagta tcaagtagtc atcggaaatg acacaactca ttatattatt   1440

gatgacttag agcctgccag caattatact ttctacattg tagcatatat gccaatggga   1500

gccagccaga tgtctgacca tgtgacacag aatactctag aggatgaccc cagaagaaaa   1560

tatcatgtga gactcctggc ttacaacaac atagacgatg gctatcaggc agatcagact   1620

gtcagcactc caggatgcgt gtctgttcgt gatcgcatgg tccctcctcc accaccaccc   1680

caccatctct atgcgaaggc taacacctca tcttccatct tcctgcactg gaggaggcct   1740

gcattcaccg ctgcacaaat cattaactac accatccgct gtaatcctgt tggcctgcag   1800

aatgcttctt tggttctgta ccttcaaaca tcagaaactc acatgttggt tcaaggtcta   1860

gaaccaaaca ccaaatacga atttgccgtt cgattacatg tggatcagct ttccagtcct   1920

tggagccctg tagtctacca ttctactctt ccagaagcac cagcaggccc accagttgga   1980

gtaaaagtga cattaataga ggatgacact gccctggttt cttggaaacc ccctgatggc   2040

ccagaaacag ttgtgacccg ctatactatc ttatatgcat ctaggaaggc ctggattgca   2100

ggagagtggc aggtcttaca ccgtgaaggg gcaataacca tggctttgct agaaaacttg   2160

gtagcaggaa atgtgtacat tgtcaagata tctgcatcca atgaggtggg agaaggaccc   2220

ttttcaaatt ctgtggagct ggcagtactt ccaaaggaaa cctctgaatc aaatcagagg   2280

cccaagcgtt tagattctgc tgatgccaaa gtttattcag gatattacca tctggaccaa   2340

aaatcaatga ctggcattgc tgtaggtgtt ggcatagcct tgacctgcat cctcatctgt   2400

gttctcatct tgatataccg aagtaaagcc aggaaatcat ctgcttccaa gacggcacag   2460

aatggaactc aacagttacc tcgtaccagt gcctccttag ctagtggaaa tgaggtagga   2520

aagaacctgg aaggagctgt aggaaatgaa gaatctttaa tgccaatgat catgccaaac   2580

agcttcattg atgcaaaggt actgagctgc gggatttgct gcataagccg ttcttccatt   2640

cctcctccct gtgtgtgtaa aatgtacttc ccccaaaatt gtatgttgaa tgtattatac   2700

caatactctt attaa                                                    2715
```

```
<210> SEQ ID NO 6
<211> LENGTH: 904
<212> TYPE: PRT
<213> ORGANISM: homo sapiens

<400> SEQUENCE: 6

Met Ala Pro Pro Leu Arg Pro Leu Ala Arg Leu Arg Pro Pro Gly Met
 1               5                  10                  15

Leu Leu Arg Ala Leu Leu Leu Leu Leu Leu Leu Ser Pro Leu Pro Gly
            20                  25                  30

Val Trp Cys Phe Ser Glu Leu Ser Phe Val Lys Glu Pro Gln Asp Val
        35                  40                  45

Thr Val Thr Arg Lys Asp Pro Val Val Leu Asp Cys Gln Ala His Gly
    50                  55                  60

Glu Val Pro Ile Lys Val Thr Trp Leu Lys Asn Gly Ala Lys Met Ser
65                  70                  75                  80

Glu Asn Lys Arg Ile Glu Val Leu Ser Asn Gly Ser Leu Tyr Ile Ser
                85                  90                  95

Glu Val Glu Gly Arg Arg Gly Glu Gln Ser Asp Glu Gly Phe Tyr Gln
            100                 105                 110

Cys Leu Ala Met Asn Lys Tyr Gly Ala Ile Leu Ser Gln Lys Ala His
        115                 120                 125

Leu Ala Leu Ser Thr Ile Ser Ala Phe Glu Val Gln Pro Ile Ser Thr
```

-continued

```
    130                 135                 140

Glu Val His Glu Gly Gly Val Ala Arg Phe Ala Cys Lys Ile Ser Ser
145                 150                 155                 160

His Pro Pro Ala Val Ile Thr Trp Glu Phe Asn Arg Thr Thr Leu Pro
                165                 170                 175

Met Thr Met Asp Arg Ile Thr Ala Leu Pro Thr Gly Val Leu Gln Ile
            180                 185                 190

Tyr Asp Val Ser Gln Arg Asp Ser Gly Asn Tyr Arg Cys Ile Ala Ala
        195                 200                 205

Thr Val Ala His Arg Arg Lys Ser Met Glu Ala Ser Leu Thr Val Ile
    210                 215                 220

Pro Ala Lys Glu Ser Lys Ser Phe His Thr Pro Thr Ile Ile Ala Gly
225                 230                 235                 240

Pro Gln Asn Ile Thr Thr Ser Leu His Gln Thr Val Val Leu Glu Cys
                245                 250                 255

Met Ala Thr Gly Asn Pro Lys Pro Ile Ile Ser Trp Ser Arg Leu Asp
            260                 265                 270

His Lys Ser Ile Asp Val Phe Asn Thr Arg Val Leu Gly Asn Gly Asn
        275                 280                 285

Leu Met Ile Ser Asp Val Arg Leu Gln His Ala Gly Val Tyr Val Cys
    290                 295                 300

Arg Ala Thr Thr Pro Gly Thr Arg Asn Phe Thr Val Ala Met Ala Thr
305                 310                 315                 320

Leu Thr Val Leu Ala Pro Pro Ser Phe Val Glu Trp Pro Glu Ser Leu
                325                 330                 335

Thr Arg Pro Arg Ala Gly Thr Ala Arg Phe Val Cys Gln Ala Glu Gly
            340                 345                 350

Ile Pro Ser Pro Lys Met Ser Trp Leu Lys Asn Gly Arg Lys Ile His
        355                 360                 365

Ser Asn Gly Arg Ile Lys Met Tyr Asn Ser Lys Leu Val Ile Asn Gln
    370                 375                 380

Ile Ile Pro Glu Asp Asp Ala Ile Tyr Gln Cys Met Ala Glu Asn Ser
385                 390                 395                 400

Gln Gly Ser Ile Leu Ser Arg Ala Arg Leu Thr Val Val Met Ser Glu
                405                 410                 415

Asp Arg Pro Ser Ala Pro Tyr Asn Val His Ala Glu Thr Met Ser Ser
            420                 425                 430

Ser Ala Ile Leu Leu Ala Trp Glu Arg Pro Leu Tyr Asn Ser Asp Lys
        435                 440                 445

Val Ile Ala Tyr Ser Val His Tyr Met Lys Ala Glu Gly Leu Asn Asn
    450                 455                 460

Glu Glu Tyr Gln Val Val Ile Gly Asn Asp Thr Thr His Tyr Ile Ile
465                 470                 475                 480

Asp Asp Leu Glu Pro Ala Ser Asn Tyr Thr Phe Tyr Ile Val Ala Tyr
                485                 490                 495

Met Pro Met Gly Ala Ser Gln Met Ser Asp His Val Thr Gln Asn Thr
            500                 505                 510

Leu Glu Asp Asp Pro Arg Arg Lys Tyr His Val Arg Leu Leu Ala Tyr
        515                 520                 525

Asn Asn Ile Asp Asp Gly Tyr Gln Ala Asp Gln Thr Val Ser Thr Pro
    530                 535                 540

Gly Cys Val Ser Val Arg Asp Arg Met Val Pro Pro Pro Pro Pro Pro
545                 550                 555                 560
```

-continued

```
His His Leu Tyr Ala Lys Ala Asn Thr Ser Ser Ser Ile Phe Leu His
                565                 570                 575

Trp Arg Arg Pro Ala Phe Thr Ala Ala Gln Ile Ile Asn Tyr Thr Ile
            580                 585                 590

Arg Cys Asn Pro Val Gly Leu Gln Asn Ala Ser Leu Val Leu Tyr Leu
        595                 600                 605

Gln Thr Ser Glu Thr His Met Leu Val Gln Gly Leu Glu Pro Asn Thr
    610                 615                 620

Lys Tyr Glu Phe Ala Val Arg Leu His Val Asp Gln Leu Ser Ser Pro
625                 630                 635                 640

Trp Ser Pro Val Val Tyr His Ser Thr Leu Pro Glu Ala Pro Ala Gly
                645                 650                 655

Pro Pro Val Gly Val Lys Val Thr Leu Ile Glu Asp Asp Thr Ala Leu
            660                 665                 670

Val Ser Trp Lys Pro Pro Asp Gly Pro Glu Thr Val Val Thr Arg Tyr
        675                 680                 685

Thr Ile Leu Tyr Ala Ser Arg Lys Ala Trp Ile Ala Gly Glu Trp Gln
    690                 695                 700

Val Leu His Arg Glu Gly Ala Ile Thr Met Ala Leu Leu Glu Asn Leu
705                 710                 715                 720

Val Ala Gly Asn Val Tyr Ile Val Lys Ile Ser Ala Ser Asn Glu Val
                725                 730                 735

Gly Glu Gly Pro Phe Ser Asn Ser Val Glu Leu Ala Val Leu Pro Lys
            740                 745                 750

Glu Thr Ser Glu Ser Asn Gln Arg Pro Lys Arg Leu Asp Ser Ala Asp
        755                 760                 765

Ala Lys Val Tyr Ser Gly Tyr Tyr His Leu Asp Gln Lys Ser Met Thr
    770                 775                 780

Gly Ile Ala Val Gly Val Gly Ile Ala Leu Thr Cys Ile Leu Ile Cys
785                 790                 795                 800

Val Leu Ile Leu Ile Tyr Arg Ser Lys Ala Arg Lys Ser Ser Ala Ser
                805                 810                 815

Lys Thr Ala Gln Asn Gly Thr Gln Gln Leu Pro Arg Thr Ser Ala Ser
            820                 825                 830

Leu Ala Ser Gly Asn Glu Val Gly Lys Asn Leu Glu Gly Ala Val Gly
        835                 840                 845

Asn Glu Glu Ser Leu Met Pro Met Ile Met Pro Asn Ser Phe Ile Asp
    850                 855                 860

Ala Lys Val Leu Ser Cys Gly Ile Cys Cys Ile Ser Arg Ser Ser Ile
865                 870                 875                 880

Pro Pro Pro Cys Val Cys Lys Met Tyr Phe Pro Gln Asn Cys Met Leu
                885                 890                 895

Asn Val Leu Tyr Gln Tyr Ser Tyr
            900

<210> SEQ ID NO 7
<211> LENGTH: 3453
<212> TYPE: DNA
<213> ORGANISM: homo sapiens

<400> SEQUENCE: 7

atggcgcctc ctctgcgacc cctcgcccgg ctgcgaccgc cggggatgct gctccgcgcg     60

ctcctgctcc tgctgmtgct cagtcctttg ccaggagtgt ggtgctttag cgaactgtct    120
```

-continued

```
tttgtaaaag aaccacagga tgtaactgtc acaagaaagg acccagtcgt tttagattgc    180
caggctcacg gagaagttcc tattaaggtc acatggttga aaaatggagc aaaaatgtct    240
gaaaataaac ggatcgaggt tctttctaac ggctctttat acatcagtga ggtggaaggc    300
aggcgaggag agcagtccga tgaaggattt tatcagtgct tggcaatgaa caaatatgga    360
gccattctta gtcaaaaagc tcatcttgcc ttatcaacta tttctgcatt tgaagtccag    420
ccaatttcca ctgaggtcca cgaaggtgga gttgctcgat ttgcatgcaa gatttcatcc    480
caccctcctg cagtcataac atgggagttc aatcggacaa ctctacctat gactatggac    540
aggataactg ccctaccaac aggagtattg cagatctatg atgtcagcca aagggattct    600
ggaaattatc gttgtattgc tgccactgta gcccaccgac gtaaaagtat ggaggcctcg    660
ctaactgtga ttccagctaa ggagtcaaaa tccttccaca caccaacaat tatagcaggt    720
ccacagaaca taacaacatc tcttcatcag actgtagttt tggaatgcat ggccacagga    780
aatcccaaac caatcatttc ttggagccgc cttgatcaca aatccattga tgtctttaat    840
actcgggtac ttggaaatgg taatctcatg atatctgatg tcaggctaca acatgctgga    900
gtatatgttt gtcgggccac tacccctggc acacgcaact ttacagttgc tatggcaact    960
ttaactgtat tagctcctcc ttcatttgtt gaatggccag aaagtttaac aaggcctcga   1020
gctggcactg ctcgatttgt gtgtcaggca gaaggaatcc cctctcccaa gatgtcatgg   1080
ttgaaaaatg gaaggaagat acattcgaat ggtagaatta aaatgtacaa cagtaaattg   1140
gtaattaacc agattattcc tgaagatgat gctatttatc agtgcatggc tgagaatagc   1200
caaggatcta ttttatctag agccagactg actgtagtga tgtcagaaga cagacccagt   1260
gctccctata atgtacatgc tgaaaccatg tcaagctcag ccattctttt agcctgggag   1320
aggccacttt ataattcaga caaagtcatt gcctattctg tacactacat gaaagcagaa   1380
ggtttaaata atgaagagta tcaagtagtc atcggaaatg acacaactca ttatattatt   1440
gatgacttag agcctgccag caattatact ttctacattg tagcatatat gccaatggga   1500
gccagccaga tgtctgacca tgtgacacag aatactctag aggatgttcc cctgagacct   1560
cctgaaatta gtttgacaag tcgaagtccc actgatattc tcatctcctg gctgccaatc   1620
ccagccaaat atcggcgggg ccaagtggtg ctgtatcgct tgtctttccg cctaagtact   1680
gagaattcaa tccaagttct ggagctcccg gggaccacgc atgagtacct tttggaaggc   1740
ctgaaacctg acagtgtcta cctggttcgg attactgctg ccaccagagt ggggctggga   1800
gagtcatcag tatggacttc acataggacg cccaaagcta caagcgtgaa agcccctaag   1860
tctccagagt tgcatttgga gcctctgaac tgtaccacca tttctgtgag gtggcagcaa   1920
gatgtagagg acacagctgc tattcagggc tacaagctgt actacaagga agaagggcag   1980
caggagaatg ggcccatttt cttggatacc aaggacctac tctatactct cagtggctta   2040
gaccccagaa gaaaatatca tgtgagactc ctggcttaca acaacataga cgatggctat   2100
caggcagatc agactgtcag cactccagga tgcgtgtctg ttcgtgatcg catggtccct   2160
cctccaccac caccccacca tctctatgcg aaggctaaca cctcatcttc catcttcctg   2220
cactggagga ggcctgcatt caccgctgca caaatcatta actacaccat ccgctgtaat   2280
cctgttggcc tgcagaatgc ttctttggtt ctgtaccttc aaacatcaga aactcacatg   2340
ttggttcaag gtctagaacc aaacaccaaa tacgaatttg ccgttcgatt acatgtggat   2400
cagctttcca gtccttggag ccctgtagtc taccattcta ctcttccaga agcaccagca   2460
ggcccaccag ttggagtaaa agtgacatta atagaggatg acactgccct ggtttcttgg   2520
```

```
aaaccccctg atggcccaga aacagttgtg acccgctata ctatcttata tgcatctagg   2580

aaggcctgga ttgcaggaga gtggcaggtc ttacaccgtg aaggggcaat aaccatggct   2640

ttgctagaaa acttggtagc aggaaatgtg tacattgtca agatatctgc atccaatgag   2700

gtgggagaag gacccttttc aaattctgtg gagctggcag tacttccaaa ggaaacctct   2760

gaatcaaatc agaggcccaa gcgtttagat tctgctgatg ccaaagttta ttcaggatat   2820

taccatctgg accaaaaatc aatgactggc attgctgtag gtgttggcat agccttgacc   2880

tgcatcctca tctgtgttct catcttgata taccgaagta aagccaggaa atcatctgct   2940

tccaagacgg cacagaatgg aactcaacag ttacctcgta ccagtgcctc cttagctagt   3000

ggaaatgagg taggaaagaa cctggaagga gctgtaggaa atgaagaatc tttaatgcca   3060

atgatcatgc caaacagctt cattgatgca aagggaggaa ctgacctgat aattaatagc   3120

tatggtccta taattaaaaa caactctaag aaaaagtggt ttttttcca agactcaaag    3180

aagatacaag ttgagcagcc tcaaagaaga tttactccag cggtctgctt ttaccagcca   3240

ggcaccactg tattaatcag tgatgaagac tcccctagct ccccaggtca gacaaccagc   3300

ttctcaagac cctttggtgt tgcagctgat acagaacatt cagcaaatag tgaaggcagc   3360

catgagactg ggattctgg gcggttttct catgagtcca acgatgagat acatctgtcc    3420

tcagttataa gtaccacacc ccccaacctc tga                                3453
```

```
<210> SEQ ID NO 8
<211> LENGTH: 1150
<212> TYPE: PRT
<213> ORGANISM: homo sapiens

<400> SEQUENCE: 8

Met Ala Pro Pro Leu Arg Pro Leu Ala Arg Leu Arg Pro Pro Gly Met
 1               5                  10                  15

Leu Leu Arg Ala Leu Leu Leu Leu Leu Leu Leu Ser Pro Leu Pro Gly
            20                  25                  30

Val Trp Cys Phe Ser Glu Leu Ser Phe Val Lys Glu Pro Gln Asp Val
        35                  40                  45

Thr Val Thr Arg Lys Asp Pro Val Val Leu Asp Cys Gln Ala His Gly
    50                  55                  60

Glu Val Pro Ile Lys Val Thr Trp Leu Lys Asn Gly Ala Lys Met Ser
65                  70                  75                  80

Glu Asn Lys Arg Ile Glu Val Leu Ser Asn Gly Ser Leu Tyr Ile Ser
                85                  90                  95

Glu Val Glu Gly Arg Arg Gly Glu Gln Ser Asp Glu Gly Phe Tyr Gln
            100                 105                 110

Cys Leu Ala Met Asn Lys Tyr Gly Ala Ile Leu Ser Gln Lys Ala His
        115                 120                 125

Leu Ala Leu Ser Thr Ile Ser Ala Phe Glu Val Gln Pro Ile Ser Thr
    130                 135                 140

Glu Val His Glu Gly Gly Val Ala Arg Phe Ala Cys Lys Ile Ser Ser
145                 150                 155                 160

His Pro Pro Ala Val Ile Thr Trp Glu Phe Asn Arg Thr Thr Leu Pro
                165                 170                 175

Met Thr Met Asp Arg Ile Thr Ala Leu Pro Thr Gly Val Leu Gln Ile
            180                 185                 190

Tyr Asp Val Ser Gln Arg Asp Ser Gly Asn Tyr Arg Cys Ile Ala Ala
        195                 200                 205
```

-continued

```
Thr Val Ala His Arg Arg Lys Ser Met Glu Ala Ser Leu Thr Val Ile
    210                 215                 220

Pro Ala Lys Glu Ser Lys Ser Phe His Thr Pro Thr Ile Ile Ala Gly
225                 230                 235                 240

Pro Gln Asn Ile Thr Thr Ser Leu His Gln Thr Val Val Leu Glu Cys
                245                 250                 255

Met Ala Thr Gly Asn Pro Lys Pro Ile Ile Ser Trp Ser Arg Leu Asp
            260                 265                 270

His Lys Ser Ile Asp Val Phe Asn Thr Arg Val Leu Gly Asn Gly Asn
        275                 280                 285

Leu Met Ile Ser Asp Val Arg Leu Gln His Ala Gly Val Tyr Val Cys
    290                 295                 300

Arg Ala Thr Thr Pro Gly Thr Arg Asn Phe Thr Val Ala Met Ala Thr
305                 310                 315                 320

Leu Thr Val Leu Ala Pro Pro Ser Phe Val Glu Trp Pro Glu Ser Leu
                325                 330                 335

Thr Arg Pro Arg Ala Gly Thr Ala Arg Phe Val Cys Gln Ala Glu Gly
            340                 345                 350

Ile Pro Ser Pro Lys Met Ser Trp Leu Lys Asn Gly Arg Lys Ile His
        355                 360                 365

Ser Asn Gly Arg Ile Lys Met Tyr Asn Ser Lys Leu Val Ile Asn Gln
    370                 375                 380

Ile Ile Pro Glu Asp Asp Ala Ile Tyr Gln Cys Met Ala Glu Asn Ser
385                 390                 395                 400

Gln Gly Ser Ile Leu Ser Arg Ala Arg Leu Thr Val Val Met Ser Glu
                405                 410                 415

Asp Arg Pro Ser Ala Pro Tyr Asn Val His Ala Glu Thr Met Ser Ser
            420                 425                 430

Ser Ala Ile Leu Leu Ala Trp Glu Arg Pro Leu Tyr Asn Ser Asp Lys
        435                 440                 445

Val Ile Ala Tyr Ser Val His Tyr Met Lys Ala Glu Gly Leu Asn Asn
    450                 455                 460

Glu Glu Tyr Gln Val Val Ile Gly Asn Asp Thr Thr His Tyr Ile Ile
465                 470                 475                 480

Asp Asp Leu Glu Pro Ala Ser Asn Tyr Thr Phe Tyr Ile Val Ala Tyr
                485                 490                 495

Met Pro Met Gly Ala Ser Gln Met Ser Asp His Val Thr Gln Asn Thr
            500                 505                 510

Leu Glu Asp Val Pro Leu Arg Pro Pro Glu Ile Ser Leu Thr Ser Arg
        515                 520                 525

Ser Pro Thr Asp Ile Leu Ile Ser Trp Leu Pro Ile Pro Ala Lys Tyr
    530                 535                 540

Arg Arg Gly Gln Val Val Leu Tyr Arg Leu Ser Phe Arg Leu Ser Thr
545                 550                 555                 560

Glu Asn Ser Ile Gln Val Leu Glu Leu Pro Gly Thr Thr His Glu Tyr
                565                 570                 575

Leu Leu Glu Gly Leu Lys Pro Asp Ser Val Tyr Leu Val Arg Ile Thr
            580                 585                 590

Ala Ala Thr Arg Val Gly Leu Gly Glu Ser Ser Val Trp Thr Ser His
        595                 600                 605

Arg Thr Pro Lys Ala Thr Ser Val Lys Ala Pro Lys Ser Pro Glu Leu
    610                 615                 620
```

-continued

```
His Leu Glu Pro Leu Asn Cys Thr Thr Ile Ser Val Arg Trp Gln Gln
625                 630                 635                 640

Asp Val Glu Asp Thr Ala Ala Ile Gln Gly Tyr Lys Leu Tyr Tyr Lys
                645                 650                 655

Glu Glu Gly Gln Gln Glu Asn Gly Pro Ile Phe Leu Asp Thr Lys Asp
            660                 665                 670

Leu Leu Tyr Thr Leu Ser Gly Leu Asp Pro Arg Arg Lys Tyr His Val
        675                 680                 685

Arg Leu Leu Ala Tyr Asn Asn Ile Asp Asp Gly Tyr Gln Ala Asp Gln
    690                 695                 700

Thr Val Ser Thr Pro Gly Cys Val Ser Val Arg Asp Arg Met Val Pro
705                 710                 715                 720

Pro Pro Pro Pro Pro His His Leu Tyr Ala Lys Ala Asn Thr Ser Ser
                725                 730                 735

Ser Ile Phe Leu His Trp Arg Arg Pro Ala Phe Thr Ala Ala Gln Ile
            740                 745                 750

Ile Asn Tyr Thr Ile Arg Cys Asn Pro Val Gly Leu Gln Asn Ala Ser
        755                 760                 765

Leu Val Leu Tyr Leu Gln Thr Ser Glu Thr His Met Leu Val Gln Gly
    770                 775                 780

Leu Glu Pro Asn Thr Lys Tyr Glu Phe Ala Val Arg Leu His Val Asp
785                 790                 795                 800

Gln Leu Ser Ser Pro Trp Ser Pro Val Val Tyr His Ser Thr Leu Pro
                805                 810                 815

Glu Ala Pro Ala Gly Pro Pro Val Gly Val Lys Val Thr Leu Ile Glu
            820                 825                 830

Asp Asp Thr Ala Leu Val Ser Trp Lys Pro Pro Asp Gly Pro Glu Thr
        835                 840                 845

Val Val Thr Arg Tyr Thr Ile Leu Tyr Ala Ser Arg Lys Ala Trp Ile
    850                 855                 860

Ala Gly Glu Trp Gln Val Leu His Arg Glu Gly Ala Ile Thr Met Ala
865                 870                 875                 880

Leu Leu Glu Asn Leu Val Ala Gly Asn Val Tyr Ile Val Lys Ile Ser
                885                 890                 895

Ala Ser Asn Glu Val Gly Glu Gly Pro Phe Ser Asn Ser Val Glu Leu
            900                 905                 910

Ala Val Leu Pro Lys Glu Thr Ser Glu Ser Asn Gln Arg Pro Lys Arg
        915                 920                 925

Leu Asp Ser Ala Asp Ala Lys Val Tyr Ser Gly Tyr Tyr His Leu Asp
    930                 935                 940

Gln Lys Ser Met Thr Gly Ile Ala Val Gly Val Gly Ile Ala Leu Thr
945                 950                 955                 960

Cys Ile Leu Ile Cys Val Leu Ile Leu Ile Tyr Arg Ser Lys Ala Arg
                965                 970                 975

Lys Ser Ser Ala Ser Lys Thr Ala Gln Asn Gly Thr Gln Gln Leu Pro
            980                 985                 990

Arg Thr Ser Ala Ser Leu Ala Ser Gly Asn Glu Val Gly Lys Asn Leu
        995                 1000                1005

Glu Gly Ala Val Gly Asn Glu Glu Ser Leu Met Pro Met Ile Met Pro
    1010                1015                1020

Asn Ser Phe Ile Asp Ala Lys Gly Gly Thr Asp Leu Ile Ile Asn Ser
1025                1030                1035                1040

Tyr Gly Pro Ile Ile Lys Asn Asn Ser Lys Lys Lys Trp Phe Phe Phe
```

-continued

```
                1045                1050                1055

Gln Asp Ser Lys Lys Ile Gln Val Glu Gln Pro Gln Arg Arg Phe Thr
            1060                1065                1070

Pro Ala Val Cys Phe Tyr Gln Pro Gly Thr Thr Val Leu Ile Ser Asp
        1075                1080                1085

Glu Asp Ser Pro Ser Ser Pro Gly Gln Thr Thr Ser Phe Ser Arg Pro
    1090                1095                1100

Phe Gly Val Ala Ala Asp Thr Glu His Ser Ala Asn Ser Glu Gly Ser
1105                1110                1115                1120

His Glu Thr Gly Asp Ser Gly Arg Phe Ser His Glu Ser Asn Asp Glu
                1125                1130                1135

Ile His Leu Ser Ser Val Ile Ser Thr Thr Pro Pro Asn Leu
            1140                1145                1150


<210> SEQ ID NO 9
<211> LENGTH: 2958
<212> TYPE: DNA
<213> ORGANISM: homo sapiens

<400> SEQUENCE: 9

atggcgcctc ctctgcgacc cctcgcccgg ctgcgaccgc cggggatgct gctccgcgcg     60

ctcctgctcc tgctgmtgct cagtcctttg ccaggagtgt ggtgctttag cgaactgtct    120

tttgtaaaag aaccacagga tgtaactgtc acaagaaagg acccagtcgt tttagattgc    180

caggctcacg gagaagttcc tattaaggtc acatggttga aaaatggagc aaaaatgtct    240

gaaaataaac ggatcgaggt tctttctaac ggctctttat acatcagtga ggtggaaggc    300

aggcgaggag agcagtccga tgaaggattt tatcagtgct tggcaatgaa caaatatgga    360

gccattctta gtcaaaaagc tcatcttgcc ttatcaacta tttctgcatt tgaagtccag    420

ccaatttcca ctgaggtcca cgaaggtgga gttgctcgat ttgcatgcaa gatttcatcc    480

caccctcctg cagtcataac atgggagttc aatcggacaa ctctacctat gactatggac    540

aggataactg ccctaccaac aggagtattg cagatctatg atgtcagcca aagggattct    600

ggaaattatc gttgtattgc tgccactgta gcccaccgac gtaaaagtat ggaggcctcg    660

ctaactgtga ttccagctaa ggagtcaaaa tccttccaca caccarcaat tatagcaggt    720

ccacagaaca taacaacatc tcttcatcag actgtagttt tggaatgcat ggccacagga    780

aatcccaaac caatcatttc ttggagccgc cttgatcaca aatccattga tgtctttaat    840

actcgggtac ttggaaatgg taatctcatg atatctgatg tcaggctaca acatgctgga    900

gtatatgttt gtcgggccac taccccctggc acacgcaact ttacagttgc tatggcaact    960

ttaactgtat tagctcctcc ttcatttgtt gaatggccag aaagtttaac aaggcctcga   1020

gctggcactg ctcgatttgt gtgtcaggca gaaggaatcc cctctcccaa gatgtcatgg   1080

ttgaaaaatg gaaggaagat acattcgaat ggtagaatta aaatgtacaa cagtaaattg   1140

gtaattaacc agattattcc tgaagatgat gctatttatc agtgcatggc tgagaatagc   1200

caaggatcta ttttatctag agccagactg actgtagtga tgtcagaaga cagacccagt   1260

gctccctata atgtacatgc tgaaaccatg tcaagctcag ccattctttt agcctgggag   1320

aggccacttt ataattcaga caaagtcatt gcctattctg tacactacat gaaagcagaa   1380

ggtttaaata atgaagagta tcaagtagtc atcggaaatg acacaactca ttatattatt   1440

gatgacttag agcctgccag caattatact ttctacattg tagcatatat gccaatggga   1500

gccagccaga tgtctgacca tgtgacacag aatactctag aggatgaccc cagaagaaaa   1560
```

```
tatcatgtga gactcctggc ttacaacaac atagacgatg gctatcaggc agatcagact   1620

gtcagcactc caggatgcgt gtctgttcgt gatcgcatgg tccctcctcc accaccaccc   1680

caccatctct atgcgaaggc taacacctca tcttccatct tcctgcactg gaggaggcct   1740

gcattcaccg ctgcacaaat cattaactac accatccgct gtaatcctgt tggcctgcag   1800

aatgcttctt tggttctgta ccttcaaaca tcagaaactc acatgttggt tcaaggtcta   1860

gaaccaaaca ccaaatacga atttgccgtt cgattacatg tggatcagct ttccagtcct   1920

tggagccctg tagtctacca ttctactctt ccagaagcac cagcaggccc accagttgga   1980

gtaaaagtga cattaataga ggatgacact gccctggttt cttggaaacc ccctgatggc   2040

ccagaaacag ttgtgacccg ctatactatc ttatatgcat ctaggaaggc ctggattgca   2100

ggagagtggc aggtcttaca ccgtgaaggg gcaataacca tggctttgct agaaaacttg   2160

gtagcaggaa atgtgtacat tgtcaagata tctgcatcca atgaggtggg agaaggaccc   2220

ttttcaaatt ctgtggagct ggcagtactt ccaaaggaaa cctctgaatc aaatcagagg   2280

cccaagcgtt tagattctgc tgatgccaaa gtttattcag gatattacca tctggaccaa   2340

aaatcaatga ctggcattgc tgtaggtgtt ggcatagcct tgacctgcat cctcatctgt   2400

gttctcatct tgatataccg aagtaaagcc aggaaatcat ctgcttccaa gacggcacag   2460

aatggaactc aacagttacc tcgtaccagt gcctccttag ctagtggaaa tgaggtagga   2520

aagaacctgg aaggagctgt aggaaatgaa gaatctttaa tgccaatgat catgccaaac   2580

agcttcattg atgcaaaggg aggaactgac ctgataatta atagctatgg tcctataatt   2640

aaaaacaact ctaagaaaaa gtggtttttt ttccaagact caaagaagat acaagttgag   2700

cagcctcaaa gaagatttac tccagcggtc tgcttttacc agccaggcac cactgtatta   2760

atcagtgatg aagactcccc tagctcccca ggtcagacaa ccagcttctc aagacccttt   2820

ggtgttgcag ctgatacaga acattcagca aatagtgaag gcagccatga gactggggat   2880

tctgggcggt tttctcatga gtccaacgat gagatacatc tgtcctcagt tataagtacc   2940

acacccccca acctctga                                                 2958
```

```
<210> SEQ ID NO 10
<211> LENGTH: 985
<212> TYPE: PRT
<213> ORGANISM: homo sapiens

<400> SEQUENCE: 10

Met Ala Pro Pro Leu Arg Pro Leu Ala Arg Leu Arg Pro Pro Gly Met
 1               5                  10                  15

Leu Leu Arg Ala Leu Leu Leu Leu Leu Leu Leu Ser Pro Leu Pro Gly
            20                  25                  30

Val Trp Cys Phe Ser Glu Leu Ser Phe Val Lys Glu Pro Gln Asp Val
        35                  40                  45

Thr Val Thr Arg Lys Asp Pro Val Val Leu Asp Cys Gln Ala His Gly
    50                  55                  60

Glu Val Pro Ile Lys Val Thr Trp Leu Lys Asn Gly Ala Lys Met Ser
65                  70                  75                  80

Glu Asn Lys Arg Ile Glu Val Leu Ser Asn Gly Ser Leu Tyr Ile Ser
                85                  90                  95

Glu Val Glu Gly Arg Arg Gly Glu Gln Ser Asp Glu Gly Phe Tyr Gln
            100                 105                 110

Cys Leu Ala Met Asn Lys Tyr Gly Ala Ile Leu Ser Gln Lys Ala His
```

-continued

```
        115                 120                 125

Leu Ala Leu Ser Thr Ile Ser Ala Phe Glu Val Gln Pro Ile Ser Thr
    130                 135                 140

Glu Val His Glu Gly Gly Val Ala Arg Phe Ala Cys Lys Ile Ser Ser
145                 150                 155                 160

His Pro Pro Ala Val Ile Thr Trp Glu Phe Asn Arg Thr Thr Leu Pro
                165                 170                 175

Met Thr Met Asp Arg Ile Thr Ala Leu Pro Thr Gly Val Leu Gln Ile
            180                 185                 190

Tyr Asp Val Ser Gln Arg Asp Ser Gly Asn Tyr Arg Cys Ile Ala Ala
        195                 200                 205

Thr Val Ala His Arg Arg Lys Ser Met Glu Ala Ser Leu Thr Val Ile
    210                 215                 220

Pro Ala Lys Glu Ser Lys Ser Phe His Thr Pro Thr Ile Ile Ala Gly
225                 230                 235                 240

Pro Gln Asn Ile Thr Thr Ser Leu His Gln Thr Val Val Leu Glu Cys
                245                 250                 255

Met Ala Thr Gly Asn Pro Lys Pro Ile Ile Ser Trp Ser Arg Leu Asp
            260                 265                 270

His Lys Ser Ile Asp Val Phe Asn Thr Arg Val Leu Gly Asn Gly Asn
        275                 280                 285

Leu Met Ile Ser Asp Val Arg Leu Gln His Ala Gly Val Tyr Val Cys
    290                 295                 300

Arg Ala Thr Thr Pro Gly Thr Arg Asn Phe Thr Val Ala Met Ala Thr
305                 310                 315                 320

Leu Thr Val Leu Ala Pro Pro Ser Phe Val Glu Trp Pro Glu Ser Leu
                325                 330                 335

Thr Arg Pro Arg Ala Gly Thr Ala Arg Phe Val Cys Gln Ala Glu Gly
            340                 345                 350

Ile Pro Ser Pro Lys Met Ser Trp Leu Lys Asn Gly Arg Lys Ile His
        355                 360                 365

Ser Asn Gly Arg Ile Lys Met Tyr Asn Ser Lys Leu Val Ile Asn Gln
    370                 375                 380

Ile Ile Pro Glu Asp Asp Ala Ile Tyr Gln Cys Met Ala Glu Asn Ser
385                 390                 395                 400

Gln Gly Ser Ile Leu Ser Arg Ala Arg Leu Thr Val Val Met Ser Glu
                405                 410                 415

Asp Arg Pro Ser Ala Pro Tyr Asn Val His Ala Glu Thr Met Ser Ser
            420                 425                 430

Ser Ala Ile Leu Leu Ala Trp Glu Arg Pro Leu Tyr Asn Ser Asp Lys
        435                 440                 445

Val Ile Ala Tyr Ser Val His Tyr Met Lys Ala Glu Gly Leu Asn Asn
    450                 455                 460

Glu Glu Tyr Gln Val Val Ile Gly Asn Asp Thr Thr His Tyr Ile Ile
465                 470                 475                 480

Asp Asp Leu Glu Pro Ala Ser Asn Tyr Thr Phe Tyr Ile Val Ala Tyr
                485                 490                 495

Met Pro Met Gly Ala Ser Gln Met Ser Asp His Val Thr Gln Asn Thr
            500                 505                 510

Leu Glu Asp Asp Pro Arg Arg Lys Tyr His Val Arg Leu Leu Ala Tyr
        515                 520                 525

Asn Asn Ile Asp Asp Gly Tyr Gln Ala Asp Gln Thr Val Ser Thr Pro
    530                 535                 540
```

-continued

```
Gly Cys Val Ser Val Arg Asp Arg Met Val Pro Pro Pro Pro Pro Pro
545                 550                 555                 560

His His Leu Tyr Ala Lys Ala Asn Thr Ser Ser Ser Ile Phe Leu His
                565                 570                 575

Trp Arg Arg Pro Ala Phe Thr Ala Ala Gln Ile Ile Asn Tyr Thr Ile
            580                 585                 590

Arg Cys Asn Pro Val Gly Leu Gln Asn Ala Ser Leu Val Leu Tyr Leu
        595                 600                 605

Gln Thr Ser Glu Thr His Met Leu Val Gln Gly Leu Glu Pro Asn Thr
    610                 615                 620

Lys Tyr Glu Phe Ala Val Arg Leu His Val Asp Gln Leu Ser Ser Pro
625                 630                 635                 640

Trp Ser Pro Val Val Tyr His Ser Thr Leu Pro Glu Ala Pro Ala Gly
                645                 650                 655

Pro Pro Val Gly Val Lys Val Thr Leu Ile Glu Asp Asp Thr Ala Leu
            660                 665                 670

Val Ser Trp Lys Pro Pro Asp Gly Pro Glu Thr Val Val Thr Arg Tyr
        675                 680                 685

Thr Ile Leu Tyr Ala Ser Arg Lys Ala Trp Ile Ala Gly Glu Trp Gln
    690                 695                 700

Val Leu His Arg Glu Gly Ala Ile Thr Met Ala Leu Leu Glu Asn Leu
705                 710                 715                 720

Val Ala Gly Asn Val Tyr Ile Val Lys Ile Ser Ala Ser Asn Glu Val
                725                 730                 735

Gly Glu Gly Pro Phe Ser Asn Ser Val Glu Leu Ala Val Leu Pro Lys
            740                 745                 750

Glu Thr Ser Glu Ser Asn Gln Arg Pro Lys Arg Leu Asp Ser Ala Asp
        755                 760                 765

Ala Lys Val Tyr Ser Gly Tyr Tyr His Leu Asp Gln Lys Ser Met Thr
    770                 775                 780

Gly Ile Ala Val Gly Val Gly Ile Ala Leu Thr Cys Ile Leu Ile Cys
785                 790                 795                 800

Val Leu Ile Leu Ile Tyr Arg Ser Lys Ala Arg Lys Ser Ser Ala Ser
                805                 810                 815

Lys Thr Ala Gln Asn Gly Thr Gln Gln Leu Pro Arg Thr Ser Ala Ser
            820                 825                 830

Leu Ala Ser Gly Asn Glu Val Gly Lys Asn Leu Glu Gly Ala Val Gly
        835                 840                 845

Asn Glu Glu Ser Leu Met Pro Met Ile Met Pro Asn Ser Phe Ile Asp
    850                 855                 860

Ala Lys Gly Gly Thr Asp Leu Ile Ile Asn Ser Tyr Gly Pro Ile Ile
865                 870                 875                 880

Lys Asn Asn Ser Lys Lys Lys Trp Phe Phe Phe Gln Asp Ser Lys Lys
                885                 890                 895

Ile Gln Val Glu Gln Pro Gln Arg Arg Phe Thr Pro Ala Val Cys Phe
            900                 905                 910

Tyr Gln Pro Gly Thr Thr Val Leu Ile Ser Asp Glu Asp Ser Pro Ser
        915                 920                 925

Ser Pro Gly Gln Thr Thr Ser Phe Ser Arg Pro Phe Gly Val Ala Ala
    930                 935                 940

Asp Thr Glu His Ser Ala Asn Ser Glu Gly Ser His Glu Thr Gly Asp
945                 950                 955                 960
```

-continued

```
Ser Gly Arg Phe Ser His Glu Ser Asn Asp Glu Ile His Leu Ser Ser
            965                 970                 975

Val Ile Ser Thr Thr Pro Pro Asn Leu
        980                 985


<210> SEQ ID NO 11
<211> LENGTH: 2976
<212> TYPE: DNA
<213> ORGANISM: homo sapiens

<400> SEQUENCE: 11

atgtctgaaa ataaacggat cgaggttctt tctaacggct ctttatacat cagtgaggtg     60

gaaggcaggc gaggagagca gtccgatgaa ggattttatc agtgcttggc aatgaacaaa    120

tatggagcca ttcttagtca aaaagctcat cttgccttat caactatttc tgcatttgaa    180

gtccagccaa tttccactga ggtccacgaa ggtggagttg ctcgatttgc atgcaagatt    240

tcatcccacc ctcctgcagt cataacatgg gagttcaatc ggacaactct acctatgact    300

atggacagga taactgccct accaacagga gtattgcaga tctatgatgt cagccaaagg    360

gattctggaa attatcgttg tattgctgcc actgtagccc accgacgtaa aagtatggag    420

gcctcgctaa ctgtgattcc agctaaggag tcaaaatcct tccacacacc arcaattata    480

gcaggtccac agaacataac aacatctctt catcagactg tagttttgga atgcatggcc    540

acaggaaatc ccaaaccaat catttcttgg agccgccttg atcacaaatc cattgatgtc    600

tttaatactc gggtacttgg aaatggtaat ctcatgatat ctgatgtcag gctacaacat    660

gctggagtat atgtttgtcg ggccactacc cctggcacac gcaactttac agttgctatg    720

gcaactttaa ctgtattagc tcctccttca tttgttgaat ggccagaaag tttaacaagg    780

cctcgagctg gcactgctcg atttgtgtgt caggcagaag gaatcccctc tcccaagatg    840

tcatggttga aaaatggaag gaagatacat tcgaatggta gaattaaaat gtacaacagt    900

aaattggtaa ttaaccagat tattcctgaa gatgatgcta tttatcagtg catggctgag    960

aatagccaag gatctatttt atctagagcc agactgactg tagtgatgtc agaagacaga   1020

cccagtgctc cctataatgt acatgctgaa accatgtcaa gctcagccat tcttttagcc   1080

tgggagaggc cactttataa ttcagacaaa gtcattgcct attctgtaca ctacatgaaa   1140

gcagaaggtt taaataatga agagtatcaa gtagtcatcg gaaatgacac aactcattat   1200

attattgatg acttagagcc tgccagcaat tatacttttct acattgtagc atatatgcca   1260

atgggagcca gccagatgtc tgaccatgtg acacagaata ctctagagga tgttcccctg   1320

agacctcctg aaattagttt gacaagtcga agtcccactg atattctcat ctcctggctg   1380

ccaatcccag ccaaatatcg gcggggccaa gtggtgctgt atcgcttgtc tttccgccta   1440

agtactgaga attcaatcca agttctggag ctcccgggga ccacgcatga gtaccttttg   1500

gaaggcctga aacctgacag tgtctacctg gttcggatta ctgctgccac cagagtgggg   1560

ctgggagagt catcagtatg gacttcacat aggacgccca aagctacaag cgtgaaagcc   1620

cctaagtctc cagagttgca tttggagcct ctgaactgta ccaccatttc tgtgaggtgg   1680

cagcaagatg tagaggacac agctgctatt cagggctaca agctgtacta caaggaagaa   1740

gggcagcagg agaatgggcc cattttcttg gataccaagg acctactcta tactctcagt   1800

ggcttagacc ccagaagaaa atatcatgtg agactcctgg cttacaacaa catagacgat   1860

ggctatcagg cagatcagac tgtcagcact ccaggatgcg tgtctgttcg tgatcgcatg   1920

gtccctcctc caccaccacc ccaccatctc tatgcgaagg ctaacacctc atcttccatc   1980
```

-continued

```
ttcctgcact ggaggaggcc tgcattcacc gctgcacaaa tcattaacta caccatccgc   2040
tgtaatcctg ttggcctgca gaatgcttct ttggttctgt accttcaaac atcagaaact   2100
cacatgttgg ttcaaggtct agaaccaaac accaaatacg aatttgccgt tcgattacat   2160
gtggatcagc tttccagtcc ttggagccct gtagtctacc attctactct tccagaagca   2220
ccagcaggcc caccagttgg agtaaaagtg acattaatag aggatgacac tgccctggtt   2280
tcttggaaac cccctgatgg cccagaaaca gttgtgaccc gctatactat cttatatgca   2340
tctaggaagg cctggattgc aggagagtgg caggtcttac accgtgaagg ggcaataacc   2400
atggctttgc tagaaaactt ggtagcagga aatgtgtaca ttgtcaagat atctgcatcc   2460
aatgaggtgg gagaaggacc cttttcaaat tctgtggagc tggcagtact tccaaaggaa   2520
acctctgaat caaatcagag gcccaagcgt ttagattctg ctgatgccaa agtttattca   2580
ggatattacc atctggacca aaaatcaatg actggcattg ctgtaggtgt tggcatagcc   2640
ttgacctgca tcctcatctg tgttctcatc ttgatatacc gaagtaaagc caggaaatca   2700
tctgcttcca agacggcaca gaatggaact caacagttac ctcgtaccag tgcctcctta   2760
gctagtggaa atgaggtagg aaagaacctg gaaggagctg taggaaatga agaatcttta   2820
atgccaatga tcatgccaaa cagcttcatt gatgcaaagg tactgagctg cgggatttgc   2880
tgcataagcc gttcttccat tcctcctccc tgtgtgtgta aaatgtactt cccccaaaat   2940
tgtatgttga atgtattata ccaatactct tattaa                             2976
```

<210> SEQ ID NO 12
<211> LENGTH: 991
<212> TYPE: PRT
<213> ORGANISM: homo sapiens

<400> SEQUENCE: 12

```
Met Ser Glu Asn Lys Arg Ile Glu Val Leu Ser Asn Gly Ser Leu Tyr
 1               5                  10                  15

Ile Ser Glu Val Glu Gly Arg Arg Gly Glu Gln Ser Asp Glu Gly Phe
            20                  25                  30

Tyr Gln Cys Leu Ala Met Asn Lys Tyr Gly Ala Ile Leu Ser Gln Lys
        35                  40                  45

Ala His Leu Ala Leu Ser Thr Ile Ser Ala Phe Glu Val Gln Pro Ile
    50                  55                  60

Ser Thr Glu Val His Glu Gly Gly Val Ala Arg Phe Ala Cys Lys Ile
65                  70                  75                  80

Ser Ser His Pro Pro Ala Val Ile Thr Trp Glu Phe Asn Arg Thr Thr
                85                  90                  95

Leu Pro Met Thr Met Asp Arg Ile Thr Ala Leu Pro Thr Gly Val Leu
            100                 105                 110

Gln Ile Tyr Asp Val Ser Gln Arg Asp Ser Gly Asn Tyr Arg Cys Ile
        115                 120                 125

Ala Ala Thr Val Ala His Arg Arg Lys Ser Met Glu Ala Ser Leu Thr
    130                 135                 140

Val Ile Pro Ala Lys Glu Ser Lys Ser Phe His Thr Pro Thr Ile Ile
145                 150                 155                 160

Ala Gly Pro Gln Asn Ile Thr Thr Ser Leu His Gln Thr Val Val Leu
                165                 170                 175

Glu Cys Met Ala Thr Gly Asn Pro Lys Pro Ile Ile Ser Trp Ser Arg
            180                 185                 190
```

-continued

```
Leu Asp His Lys Ser Ile Asp Val Phe Asn Thr Arg Val Leu Gly Asn
        195                 200                 205

Gly Asn Leu Met Ile Ser Asp Val Arg Leu Gln His Ala Gly Val Tyr
    210                 215                 220

Val Cys Arg Ala Thr Thr Pro Gly Thr Arg Asn Phe Thr Val Ala Met
225                 230                 235                 240

Ala Thr Leu Thr Val Leu Ala Pro Pro Ser Phe Val Glu Trp Pro Glu
                245                 250                 255

Ser Leu Thr Arg Pro Arg Ala Gly Thr Ala Arg Phe Val Cys Gln Ala
            260                 265                 270

Glu Gly Ile Pro Ser Pro Lys Met Ser Trp Leu Lys Asn Gly Arg Lys
        275                 280                 285

Ile His Ser Asn Gly Arg Ile Lys Met Tyr Asn Ser Lys Leu Val Ile
    290                 295                 300

Asn Gln Ile Ile Pro Glu Asp Asp Ala Ile Tyr Gln Cys Met Ala Glu
305                 310                 315                 320

Asn Ser Gln Gly Ser Ile Leu Ser Arg Ala Arg Leu Thr Val Val Met
                325                 330                 335

Ser Glu Asp Arg Pro Ser Ala Pro Tyr Asn Val His Ala Glu Thr Met
            340                 345                 350

Ser Ser Ser Ala Ile Leu Leu Ala Trp Glu Arg Pro Leu Tyr Asn Ser
        355                 360                 365

Asp Lys Val Ile Ala Tyr Ser Val His Tyr Met Lys Ala Glu Gly Leu
    370                 375                 380

Asn Asn Glu Glu Tyr Gln Val Val Ile Gly Asn Asp Thr Thr His Tyr
385                 390                 395                 400

Ile Ile Asp Asp Leu Glu Pro Ala Ser Asn Tyr Thr Phe Tyr Ile Val
                405                 410                 415

Ala Tyr Met Pro Met Gly Ala Ser Gln Met Ser Asp His Val Thr Gln
            420                 425                 430

Asn Thr Leu Glu Asp Val Pro Leu Arg Pro Pro Glu Ile Ser Leu Thr
        435                 440                 445

Ser Arg Ser Pro Thr Asp Ile Leu Ile Ser Trp Leu Pro Ile Pro Ala
    450                 455                 460

Lys Tyr Arg Arg Gly Gln Val Val Leu Tyr Arg Leu Ser Phe Arg Leu
465                 470                 475                 480

Ser Thr Glu Asn Ser Ile Gln Val Leu Glu Leu Pro Gly Thr Thr His
                485                 490                 495

Glu Tyr Leu Leu Glu Gly Leu Lys Pro Asp Ser Val Tyr Leu Val Arg
            500                 505                 510

Ile Thr Ala Ala Thr Arg Val Gly Leu Gly Glu Ser Ser Val Trp Thr
        515                 520                 525

Ser His Arg Thr Pro Lys Ala Thr Ser Val Lys Ala Pro Lys Ser Pro
    530                 535                 540

Glu Leu His Leu Glu Pro Leu Asn Cys Thr Thr Ile Ser Val Arg Trp
545                 550                 555                 560

Gln Gln Asp Val Glu Asp Thr Ala Ala Ile Gln Gly Tyr Lys Leu Tyr
                565                 570                 575

Tyr Lys Glu Glu Gly Gln Gln Glu Asn Gly Pro Ile Phe Leu Asp Thr
            580                 585                 590

Lys Asp Leu Leu Tyr Thr Leu Ser Gly Leu Asp Pro Arg Arg Lys Tyr
        595                 600                 605

His Val Arg Leu Leu Ala Tyr Asn Asn Ile Asp Asp Gly Tyr Gln Ala
```

-continued

```
    610                 615                 620

Asp Gln Thr Val Ser Thr Pro Gly Cys Val Ser Val Arg Asp Arg Met
625                 630                 635                 640

Val Pro Pro Pro Pro Pro Pro His His Leu Tyr Ala Lys Ala Asn Thr
                645                 650                 655

Ser Ser Ser Ile Phe Leu His Trp Arg Arg Pro Ala Phe Thr Ala Ala
            660                 665                 670

Gln Ile Ile Asn Tyr Thr Ile Arg Cys Asn Pro Val Gly Leu Gln Asn
        675                 680                 685

Ala Ser Leu Val Leu Tyr Leu Gln Thr Ser Glu Thr His Met Leu Val
    690                 695                 700

Gln Gly Leu Glu Pro Asn Thr Lys Tyr Glu Phe Ala Val Arg Leu His
705                 710                 715                 720

Val Asp Gln Leu Ser Ser Pro Trp Ser Pro Val Val Tyr His Ser Thr
                725                 730                 735

Leu Pro Glu Ala Pro Ala Gly Pro Pro Val Gly Val Lys Val Thr Leu
            740                 745                 750

Ile Glu Asp Asp Thr Ala Leu Val Ser Trp Lys Pro Pro Asp Gly Pro
        755                 760                 765

Glu Thr Val Val Thr Arg Tyr Thr Ile Leu Tyr Ala Ser Arg Lys Ala
    770                 775                 780

Trp Ile Ala Gly Glu Trp Gln Val Leu His Arg Glu Gly Ala Ile Thr
785                 790                 795                 800

Met Ala Leu Leu Glu Asn Leu Val Ala Gly Asn Val Tyr Ile Val Lys
                805                 810                 815

Ile Ser Ala Ser Asn Glu Val Gly Glu Gly Pro Phe Ser Asn Ser Val
            820                 825                 830

Glu Leu Ala Val Leu Pro Lys Glu Thr Ser Glu Ser Asn Gln Arg Pro
        835                 840                 845

Lys Arg Leu Asp Ser Ala Asp Ala Lys Val Tyr Ser Gly Tyr Tyr His
    850                 855                 860

Leu Asp Gln Lys Ser Met Thr Gly Ile Ala Val Gly Val Gly Ile Ala
865                 870                 875                 880

Leu Thr Cys Ile Leu Ile Cys Val Leu Ile Leu Ile Tyr Arg Ser Lys
                885                 890                 895

Ala Arg Lys Ser Ser Ala Ser Lys Thr Ala Gln Asn Gly Thr Gln Gln
            900                 905                 910

Leu Pro Arg Thr Ser Ala Ser Leu Ala Ser Gly Asn Glu Val Gly Lys
        915                 920                 925

Asn Leu Glu Gly Ala Val Gly Asn Glu Glu Ser Leu Met Pro Met Ile
    930                 935                 940

Met Pro Asn Ser Phe Ile Asp Ala Lys Val Leu Ser Cys Gly Ile Cys
945                 950                 955                 960

Cys Ile Ser Arg Ser Ser Ile Pro Pro Pro Cys Val Cys Lys Met Tyr
                965                 970                 975

Phe Pro Gln Asn Cys Met Leu Asn Val Leu Tyr Gln Tyr Ser Tyr
            980                 985                 990
```

<210> SEQ ID NO 13
<211> LENGTH: 909
<212> TYPE: DNA
<213> ORGANISM: homo sapiens

<400> SEQUENCE: 13

-continued

```
atgtctgaaa ataaacggat cgaggttctt tctaacggct ctttatacat cagtgaggtg     60

gaaggcaggc gaggagagca gtccgatgaa ggattttatc agtgcttggc aatgaacaaa    120

tatggagcca ttcttagtca aaaagctcat cttgccttat caactatttc tgcatttgaa    180

gtccagccaa tttccactga ggtccacgaa ggtggagttg ctcgatttgc atgcaagatt    240

tcatcccacc ctcctgcagt cataacatgg gagttcaatc ggacaactct acctatgact    300

atggacagga taactgccct accaacagga gtattgcaga tctatgatgt cagccaaagg    360

gattctggaa attatcgttg tattgctgcc actgtagccc accgacgtaa aagtatggag    420

gcctcgctaa ctgtgattcc agctaaggag tcaaaatcct tccacacacc arcaattata    480

gcaggtccac agaacataac aacatctctt catcagactg tagttttgga atgcatggcc    540

acaggaaatc ccaaaccaat catttcttgg agccgccttg atcacaaatc cattgatgtc    600

tttaatactc gggtacttgg aaatggtaat ctcatgatat ctgatgtcag gctacaacat    660

gctggagtat atgtttgtcg ggccactacc cctggcacac gcaactttac agttgctatg    720

gcaactttaa ctgtattagc tcctccttca tttgttgaat ggccagaaag tttaacaagg    780

cctcgagctg gcactgctcg atttgtgtgt caggcagaag gaatcccctc tcccaagatg    840

tcatggttga aaaatggaag gaagatacat tcgaatggta gaattaaaat gtacaacagg    900

tttaaataa                                                            909


<210> SEQ ID NO 14
<211> LENGTH: 302
<212> TYPE: PRT
<213> ORGANISM: homo sapiens

<400> SEQUENCE: 14

Met Ser Glu Asn Lys Arg Ile Glu Val Leu Ser Asn Gly Ser Leu Tyr
 1               5                  10                  15

Ile Ser Glu Val Glu Gly Arg Arg Gly Glu Gln Ser Asp Glu Gly Phe
            20                  25                  30

Tyr Gln Cys Leu Ala Met Asn Lys Tyr Gly Ala Ile Leu Ser Gln Lys
        35                  40                  45

Ala His Leu Ala Leu Ser Thr Ile Ser Ala Phe Glu Val Gln Pro Ile
    50                  55                  60

Ser Thr Glu Val His Glu Gly Gly Val Ala Arg Phe Ala Cys Lys Ile
65                  70                  75                  80

Ser Ser His Pro Pro Ala Val Ile Thr Trp Glu Phe Asn Arg Thr Thr
                85                  90                  95

Leu Pro Met Thr Met Asp Arg Ile Thr Ala Leu Pro Thr Gly Val Leu
            100                 105                 110

Gln Ile Tyr Asp Val Ser Gln Arg Asp Ser Gly Asn Tyr Arg Cys Ile
        115                 120                 125

Ala Ala Thr Val Ala His Arg Arg Lys Ser Met Glu Ala Ser Leu Thr
    130                 135                 140

Val Ile Pro Ala Lys Glu Ser Lys Ser Phe His Thr Pro Thr Ile Ile
145                 150                 155                 160

Ala Gly Pro Gln Asn Ile Thr Thr Ser Leu His Gln Thr Val Val Leu
                165                 170                 175

Glu Cys Met Ala Thr Gly Asn Pro Lys Pro Ile Ile Ser Trp Ser Arg
            180                 185                 190

Leu Asp His Lys Ser Ile Asp Val Phe Asn Thr Arg Val Leu Gly Asn
        195                 200                 205
```

-continued

```
Gly Asn Leu Met Ile Ser Asp Val Arg Leu Gln His Ala Gly Val Tyr
    210                 215                 220

Val Cys Arg Ala Thr Thr Pro Gly Thr Arg Asn Phe Thr Val Ala Met
225                 230                 235                 240

Ala Thr Leu Thr Val Leu Ala Pro Pro Ser Phe Val Glu Trp Pro Glu
                245                 250                 255

Ser Leu Thr Arg Pro Arg Ala Gly Thr Ala Arg Phe Val Cys Gln Ala
            260                 265                 270

Glu Gly Ile Pro Ser Pro Lys Met Ser Trp Leu Lys Asn Gly Arg Lys
        275                 280                 285

Ile His Ser Asn Gly Arg Ile Lys Met Tyr Asn Arg Phe Lys
    290                 295                 300
```

```
<210> SEQ ID NO 15
<211> LENGTH: 2481
<212> TYPE: DNA
<213> ORGANISM: homo sapiens

<400> SEQUENCE: 15

atgtctgaaa ataaacggat cgaggttctt tctaacggct ctttatacat cagtgaggtg     60

gaaggcaggc gaggagagca gtccgatgaa ggattttatc agtgcttggc aatgaacaaa    120

tatggagcca ttcttagtca aaaagctcat cttgccttat caactatttc tgcatttgaa    180

gtccagccaa tttccactga ggtccacgaa ggtggagttg ctcgatttgc atgcaagatt    240

tcatcccacc ctcctgcagt cataacatgg gagttcaatc ggacaactct acctatgact    300

atggacagga taactgccct accaacagga gtattgcaga tctatgatgt cagccaaagg    360

gattctggaa attatcgttg tattgctgcc actgtagccc accgacgtaa aagtatggag    420

gcctcgctaa ctgtgattcc agctaaggag tcaaaatcct tccacacacc arcaattata    480

gcaggtccac agaacataac aacatctctt catcagactg tagttttgga atgcatggcc    540

acaggaaatc ccaaaccaat catttcttgg agccgccttg atcacaaatc cattgatgtc    600

tttaatactc gggtacttgg aaatggtaat ctcatgatat ctgatgtcag gctacaacat    660

gctggagtat atgtttgtcg ggccactacc cctggcacac gcaactttac agttgctatg    720

gcaactttaa ctgtattagc tcctccttca tttgttgaat ggccagaaag tttaacaagg    780

cctcgagctg gcactgctcg atttgtgtgt caggcagaag gaatcccctc tcccaagatg    840

tcatggttga aaaatggaag gaagatacat tcgaatggta gaattaaaat gtacaacagt    900

aaattggtaa ttaaccagat tattcctgaa gatgatgcta tttatcagtg catggctgag    960

aatagccaag gatctatttt atctagagcc agactgactg tagtgatgtc agaagacaga   1020

cccagtgctc cctataatgt acatgctgaa accatgtcaa gctcagccat tcttttagcc   1080

tgggagaggc cactttataa ttcagacaaa gtcattgcct attctgtaca ctacatgaaa   1140

gcagaaggtt taaataatga agagtatcaa gtagtcatcg gaaatgacac aactcattat   1200

attattgatg acttagagcc tgccagcaat tatactttct acattgtagc atatatgcca   1260

atgggagcca gccagatgtc tgaccatgtg acacagaata ctctagagga tgaccccaga   1320

agaaaatatc atgtgagact cctggcttac aacaacatag acgatggcta tcaggcagat   1380

cagactgtca gcactccagg atgcgtgtct gttcgtgatc gcatggtccc tcctccacca   1440

ccaccccacc atctctatgc gaaggctaac acctcatctt ccatcttcct gcactggagg   1500

aggcctgcat tcaccgctgc acaaatcatt aactacacca tccgctgtaa tcctgttggc   1560

ctgcagaatg cttctttggt tctgtacctt caaacatcag aaactcacat gttggttcaa   1620
```

```
ggtctagaac caaacaccaa atacgaattt gccgttcgat tacatgtgga tcagctttcc   1680

agtccttgga gccctgtagt ctaccattct actcttccag aagcaccagc aggcccacca   1740

gttggagtaa aagtgacatt aatagaggat gacactgccc tggtttcttg gaaacccct    1800

gatggcccag aaacagttgt gacccgctat actatcttat atgcatctag gaaggcctgg   1860

attgcaggag agtggcaggt cttacaccgt gaaggggcaa taaccatggc tttgctagaa   1920

aacttggtag caggaaatgt gtacattgtc aagatatctg catccaatga ggtgggagaa   1980

ggaccctttt caaattctgt ggagctggca gtacttccaa aggaaacctc tgaatcaaat   2040

cagaggccca agcgtttaga ttctgctgat gccaaagttt attcaggata ttaccatctg   2100

gaccaaaaat caatgactgg cattgctgta ggtgttggca tagccttgac ctgcatcctc   2160

atctgtgttc tcatcttgat ataccgaagt aaagccagga aatcatctgc ttccaagacg   2220

gcacagaatg gaactcaaca gttacctcgt accagtgcct ccttagctag tggaaatgag   2280

gtaggaaaga acctggaagg agctgtagga aatgaagaat ctttaatgcc aatgatcatg   2340

ccaaacagct tcattgatgc aaaggtactg agctgcggga tttgctgcat aagccgttct   2400

tccattcctc ctccctgtgt gtgtaaaatg tacttccccc aaaattgtat gttgaatgta   2460

ttataccaat actcttatta a                                             2481
```

```
<210> SEQ ID NO 16
<211> LENGTH: 826
<212> TYPE: PRT
<213> ORGANISM: homo sapiens

<400> SEQUENCE: 16

Met Ser Glu Asn Lys Arg Ile Glu Val Leu Ser Asn Gly Ser Leu Tyr
 1               5                  10                  15

Ile Ser Glu Val Glu Gly Arg Arg Gly Glu Gln Ser Asp Glu Gly Phe
            20                  25                  30

Tyr Gln Cys Leu Ala Met Asn Lys Tyr Gly Ala Ile Leu Ser Gln Lys
        35                  40                  45

Ala His Leu Ala Leu Ser Thr Ile Ser Ala Phe Glu Val Gln Pro Ile
    50                  55                  60

Ser Thr Glu Val His Glu Gly Gly Val Ala Arg Phe Ala Cys Lys Ile
65                  70                  75                  80

Ser Ser His Pro Pro Ala Val Ile Thr Trp Glu Phe Asn Arg Thr Thr
                85                  90                  95

Leu Pro Met Thr Met Asp Arg Ile Thr Ala Leu Pro Thr Gly Val Leu
            100                 105                 110

Gln Ile Tyr Asp Val Ser Gln Arg Asp Ser Gly Asn Tyr Arg Cys Ile
        115                 120                 125

Ala Ala Thr Val Ala His Arg Arg Lys Ser Met Glu Ala Ser Leu Thr
    130                 135                 140

Val Ile Pro Ala Lys Glu Ser Lys Ser Phe His Thr Pro Thr Ile Ile
145                 150                 155                 160

Ala Gly Pro Gln Asn Ile Thr Thr Ser Leu His Gln Thr Val Val Leu
                165                 170                 175

Glu Cys Met Ala Thr Gly Asn Pro Lys Pro Ile Ile Ser Trp Ser Arg
            180                 185                 190

Leu Asp His Lys Ser Ile Asp Val Phe Asn Thr Arg Val Leu Gly Asn
        195                 200                 205

Gly Asn Leu Met Ile Ser Asp Val Arg Leu Gln His Ala Gly Val Tyr
```

-continued

```
    210                 215                 220

Val Cys Arg Ala Thr Thr Pro Gly Thr Arg Asn Phe Thr Val Ala Met
225                 230                 235                 240

Ala Thr Leu Thr Val Leu Ala Pro Pro Ser Phe Val Glu Trp Pro Glu
                245                 250                 255

Ser Leu Thr Arg Pro Arg Ala Gly Thr Ala Arg Phe Val Cys Gln Ala
            260                 265                 270

Glu Gly Ile Pro Ser Pro Lys Met Ser Trp Leu Lys Asn Gly Arg Lys
        275                 280                 285

Ile His Ser Asn Gly Arg Ile Lys Met Tyr Asn Ser Lys Leu Val Ile
    290                 295                 300

Asn Gln Ile Ile Pro Glu Asp Asp Ala Ile Tyr Gln Cys Met Ala Glu
305                 310                 315                 320

Asn Ser Gln Gly Ser Ile Leu Ser Arg Ala Arg Leu Thr Val Val Met
                325                 330                 335

Ser Glu Asp Arg Pro Ser Ala Pro Tyr Asn Val His Ala Glu Thr Met
            340                 345                 350

Ser Ser Ser Ala Ile Leu Leu Ala Trp Glu Arg Pro Leu Tyr Asn Ser
        355                 360                 365

Asp Lys Val Ile Ala Tyr Ser Val His Tyr Met Lys Ala Glu Gly Leu
    370                 375                 380

Asn Asn Glu Glu Tyr Gln Val Val Ile Gly Asn Asp Thr Thr His Tyr
385                 390                 395                 400

Ile Ile Asp Asp Leu Glu Pro Ala Ser Asn Tyr Thr Phe Tyr Ile Val
                405                 410                 415

Ala Tyr Met Pro Met Gly Ala Ser Gln Met Ser Asp His Val Thr Gln
            420                 425                 430

Asn Thr Leu Glu Asp Asp Pro Arg Arg Lys Tyr His Val Arg Leu Leu
        435                 440                 445

Ala Tyr Asn Asn Ile Asp Asp Gly Tyr Gln Ala Asp Gln Thr Val Ser
    450                 455                 460

Thr Pro Gly Cys Val Ser Val Arg Asp Arg Met Val Pro Pro Pro Pro
465                 470                 475                 480

Pro Pro His His Leu Tyr Ala Lys Ala Asn Thr Ser Ser Ser Ile Phe
                485                 490                 495

Leu His Trp Arg Arg Pro Ala Phe Thr Ala Ala Gln Ile Ile Asn Tyr
            500                 505                 510

Thr Ile Arg Cys Asn Pro Val Gly Leu Gln Asn Ala Ser Leu Val Leu
        515                 520                 525

Tyr Leu Gln Thr Ser Glu Thr His Met Leu Val Gln Gly Leu Glu Pro
    530                 535                 540

Asn Thr Lys Tyr Glu Phe Ala Val Arg Leu His Val Asp Gln Leu Ser
545                 550                 555                 560

Ser Pro Trp Ser Pro Val Val Tyr His Ser Thr Leu Pro Glu Ala Pro
                565                 570                 575

Ala Gly Pro Pro Val Gly Val Lys Val Thr Leu Ile Glu Asp Asp Thr
            580                 585                 590

Ala Leu Val Ser Trp Lys Pro Pro Asp Gly Pro Glu Thr Val Val Thr
        595                 600                 605

Arg Tyr Thr Ile Leu Tyr Ala Ser Arg Lys Ala Trp Ile Ala Gly Glu
    610                 615                 620

Trp Gln Val Leu His Arg Glu Gly Ala Ile Thr Met Ala Leu Leu Glu
625                 630                 635                 640
```

-continued

```
Asn Leu Val Ala Gly Asn Val Tyr Ile Val Lys Ile Ser Ala Ser Asn
                645                 650                 655

Glu Val Gly Glu Gly Pro Phe Ser Asn Ser Val Glu Leu Ala Val Leu
            660                 665                 670

Pro Lys Glu Thr Ser Glu Ser Asn Gln Arg Pro Lys Arg Leu Asp Ser
        675                 680                 685

Ala Asp Ala Lys Val Tyr Ser Gly Tyr Tyr His Leu Asp Gln Lys Ser
    690                 695                 700

Met Thr Gly Ile Ala Val Gly Val Gly Ile Ala Leu Thr Cys Ile Leu
705                 710                 715                 720

Ile Cys Val Leu Ile Leu Ile Tyr Arg Ser Lys Ala Arg Lys Ser Ser
                725                 730                 735

Ala Ser Lys Thr Ala Gln Asn Gly Thr Gln Gln Leu Pro Arg Thr Ser
            740                 745                 750

Ala Ser Leu Ala Ser Gly Asn Glu Val Gly Lys Asn Leu Glu Gly Ala
        755                 760                 765

Val Gly Asn Glu Glu Ser Leu Met Pro Met Ile Met Pro Asn Ser Phe
    770                 775                 780

Ile Asp Ala Lys Val Leu Ser Cys Gly Ile Cys Cys Ile Ser Arg Ser
785                 790                 795                 800

Ser Ile Pro Pro Pro Cys Val Cys Lys Met Tyr Phe Pro Gln Asn Cys
                805                 810                 815

Met Leu Asn Val Leu Tyr Gln Tyr Ser Tyr
            820                 825
```

<210> SEQ ID NO 17
<211> LENGTH: 3219
<212> TYPE: DNA
<213> ORGANISM: homo sapiens

<400> SEQUENCE: 17

```
atgtctgaaa ataaacggat cgaggttctt tctaacggct ctttatacat cagtgaggtg     60

gaaggcaggc gaggagagca gtccgatgaa ggattttatc agtgcttggc aatgaacaaa    120

tatggagcca ttcttagtca aaaagctcat cttgccttat caactatttc tgcatttgaa    180

gtccagccaa tttccactga ggtccacgaa ggtggagttg ctcgatttgc atgcaagatt    240

tcatcccacc ctcctgcagt cataacatgg gagttcaatc ggacaactct acctatgact    300

atggacagga taactgccct accaacagga gtattgcaga tctatgatgt cagccaaagg    360

gattctggaa attatcgttg tattgctgcc actgtagccc accgacgtaa aagtatggag    420

gcctcgctaa ctgtgattcc agctaaggag tcaaaatcct tccacacacc arcaattata    480

gcaggtccac agaacataac aacatctctt catcagactg tagttttgga atgcatggcc    540

acaggaaatc ccaaaccaat catttcttgg agccgccttg atcacaaatc cattgatgtc    600

tttaatactc gggtacttgg aaatggtaat ctcatgatat ctgatgtcag gctacaacat    660

gctggagtat atgtttgtcg ggccactacc cctggcacac gcaactttac agttgctatg    720

gcaactttaa ctgtattagc tcctccttca tttgttgaat ggccagaaag tttaacaagg    780

cctcgagctg gcactgctcg atttgtgtgt caggcagaag gaatcccctc tcccaagatg    840

tcatggttga aaaatggaag gaagatacat tcgaatggta gaattaaaat gtacaacagt    900

aaattggtaa ttaaccagat tattcctgaa gatgatgcta tttatcagtg catggctgag    960

aatagccaag gatctatttt atctagagcc agactgactg tagtgatgtc agaagacaga   1020
```

-continued

```
cccagtgctc cctataatgt acatgctgaa accatgtcaa gctcagccat tcttttagcc   1080
tgggagaggc cactttataa ttcagacaaa gtcattgcct attctgtaca ctacatgaaa   1140
gcagaaggtt taaataatga agagtatcaa gtagtcatcg gaaatgacac aactcattat   1200
attattgatg acttagagcc tgccagcaat tatactttct acattgtagc atatatgcca   1260
atgggagcca gccagatgtc tgaccatgtg acacagaata ctctagagga tgttcccctg   1320
agacctcctg aaattagttt gacaagtcga agtcccactg atattctcat ctcctggctg   1380
ccaatcccag ccaaatatcg gcggggccaa gtggtgctgt atcgcttgtc tttccgccta   1440
agtactgaga attcaatcca agttctggag ctcccgggga ccacgcatga gtaccttttg   1500
gaaggcctga aacctgacag tgtctacctg gttcggatta ctgctgccac cagagtgggg   1560
ctgggagagt catcagtatg gacttcacat aggacgccca aagctacaag cgtgaaagcc   1620
cctaagtctc cagagttgca tttggagcct ctgaactgta ccaccatttc tgtgaggtgg   1680
cagcaagatg tagaggacac agctgctatt cagggctaca agctgtacta caaggaagaa   1740
gggcagcagg agaatgggcc cattttcttg gataccaagg acctactcta tactctcagt   1800
ggcttagacc ccagaagaaa atatcatgtg agactcctgg cttacaacaa catagacgat   1860
ggctatcagg cagatcagac tgtcagcact ccaggatgcg tgtctgttcg tgatcgcatg   1920
gtccctcctc caccaccacc ccaccatctc tatgcgaagg ctaacacctc atcttccatc   1980
ttcctgcact ggaggaggcc tgcattcacc gctgcacaaa tcattaacta caccatccgc   2040
tgtaatcctg ttggcctgca gaatgcttct ttggttctgt accttcaaac atcagaaact   2100
cacatgttgg ttcaaggtct agaaccaaac accaaatacg aatttgccgt tcgattacat   2160
gtggatcagc tttccagtcc ttggagccct gtagtctacc attctactct tccagaagca   2220
ccagcaggcc caccagttgg agtaaaagtg acattaatag aggatgacac tgccctggtt   2280
tcttggaaac cccctgatgg cccagaaaca gttgtgaccc gctatactat cttatatgca   2340
tctaggaagg cctggattgc aggagagtgg caggtcttac accgtgaagg ggcaataacc   2400
atggctttgc tagaaaactt ggtagcagga aatgtgtaca ttgtcaagat atctgcatcc   2460
aatgaggtgg gagaaggacc cttttcaaat tctgtggagc tggcagtact tccaaaggaa   2520
acctctgaat caaatcagag gcccaagcgt ttagattctg ctgatgccaa agtttattca   2580
ggatattacc atctggacca aaaatcaatg actggcattg ctgtaggtgt tggcatagcc   2640
ttgacctgca tcctcatctg tgttctcatc ttgatatacc gaagtaaagc caggaaatca   2700
tctgcttcca agacggcaca gaatggaact caacagttac ctcgtaccag tgcctcctta   2760
gctagtggaa atgaggtagg aaagaacctg gaaggagctg taggaaatga agaatcttta   2820
atgccaatga tcatgccaaa cagcttcatt gatgcaaagg gaggaactga cctgataatt   2880
aatagctatg gtcctataat taaaaacaac tctaagaaaa agtggttttt tttccaagac   2940
tcaaagaaga tacaagttga gcagcctcaa agaagattta ctccagcggt ctgcttttac   3000
cagccaggca ccactgtatt aatcagtgat gaagactccc ctagctcccc aggtcagaca   3060
accagcttct caagaccctt tggtgttgca gctgatacag aacattcagc aaatagtgaa   3120
ggcagccatg agactgggga ttctgggcgg ttttctcatg agtccaacga tgagatacat   3180
ctgtcctcag ttataagtac cacacccccc aacctctga                          3219
```

<210> SEQ ID NO 18
<211> LENGTH: 1072
<212> TYPE: PRT
<213> ORGANISM: homo sapiens

<400> SEQUENCE: 18

```
Met Ser Glu Asn Lys Arg Ile Glu Val Leu Ser Asn Gly Ser Leu Tyr
 1               5                  10                  15

Ile Ser Glu Val Glu Gly Arg Arg Gly Glu Gln Ser Asp Glu Gly Phe
            20                  25                  30

Tyr Gln Cys Leu Ala Met Asn Lys Tyr Gly Ala Ile Leu Ser Gln Lys
        35                  40                  45

Ala His Leu Ala Leu Ser Thr Ile Ser Ala Phe Glu Val Gln Pro Ile
    50                  55                  60

Ser Thr Glu Val His Glu Gly Gly Val Ala Arg Phe Ala Cys Lys Ile
65                  70                  75                  80

Ser Ser His Pro Pro Ala Val Ile Thr Trp Glu Phe Asn Arg Thr Thr
                85                  90                  95

Leu Pro Met Thr Met Asp Arg Ile Thr Ala Leu Pro Thr Gly Val Leu
            100                 105                 110

Gln Ile Tyr Asp Val Ser Gln Arg Asp Ser Gly Asn Tyr Arg Cys Ile
        115                 120                 125

Ala Ala Thr Val Ala His Arg Arg Lys Ser Met Glu Ala Ser Leu Thr
    130                 135                 140

Val Ile Pro Ala Lys Glu Ser Lys Ser Phe His Thr Pro Thr Ile Ile
145                 150                 155                 160

Ala Gly Pro Gln Asn Ile Thr Thr Ser Leu His Gln Thr Val Val Leu
                165                 170                 175

Glu Cys Met Ala Thr Gly Asn Pro Lys Pro Ile Ile Ser Trp Ser Arg
            180                 185                 190

Leu Asp His Lys Ser Ile Asp Val Phe Asn Thr Arg Val Leu Gly Asn
        195                 200                 205

Gly Asn Leu Met Ile Ser Asp Val Arg Leu Gln His Ala Gly Val Tyr
    210                 215                 220

Val Cys Arg Ala Thr Thr Pro Gly Thr Arg Asn Phe Thr Val Ala Met
225                 230                 235                 240

Ala Thr Leu Thr Val Leu Ala Pro Pro Ser Phe Val Glu Trp Pro Glu
                245                 250                 255

Ser Leu Thr Arg Pro Arg Ala Gly Thr Ala Arg Phe Val Cys Gln Ala
            260                 265                 270

Glu Gly Ile Pro Ser Pro Lys Met Ser Trp Leu Lys Asn Gly Arg Lys
        275                 280                 285

Ile His Ser Asn Gly Arg Ile Lys Met Tyr Asn Ser Lys Leu Val Ile
    290                 295                 300

Asn Gln Ile Ile Pro Glu Asp Asp Ala Ile Tyr Gln Cys Met Ala Glu
305                 310                 315                 320

Asn Ser Gln Gly Ser Ile Leu Ser Arg Ala Arg Leu Thr Val Val Met
                325                 330                 335

Ser Glu Asp Arg Pro Ser Ala Pro Tyr Asn Val His Ala Glu Thr Met
            340                 345                 350

Ser Ser Ser Ala Ile Leu Leu Ala Trp Glu Arg Pro Leu Tyr Asn Ser
        355                 360                 365

Asp Lys Val Ile Ala Tyr Ser Val His Tyr Met Lys Ala Glu Gly Leu
    370                 375                 380

Asn Asn Glu Glu Tyr Gln Val Val Ile Gly Asn Asp Thr Thr His Tyr
385                 390                 395                 400

Ile Ile Asp Asp Leu Glu Pro Ala Ser Asn Tyr Thr Phe Tyr Ile Val
```

-continued

```
                405                 410                 415

Ala Tyr Met Pro Met Gly Ala Ser Gln Met Ser Asp His Val Thr Gln
            420                 425                 430

Asn Thr Leu Glu Asp Val Pro Leu Arg Pro Pro Glu Ile Ser Leu Thr
        435                 440                 445

Ser Arg Ser Pro Thr Asp Ile Leu Ile Ser Trp Leu Pro Ile Pro Ala
    450                 455                 460

Lys Tyr Arg Arg Gly Gln Val Val Leu Tyr Arg Leu Ser Phe Arg Leu
465                 470                 475                 480

Ser Thr Glu Asn Ser Ile Gln Val Leu Glu Leu Pro Gly Thr Thr His
                485                 490                 495

Glu Tyr Leu Leu Glu Gly Leu Lys Pro Asp Ser Val Tyr Leu Val Arg
            500                 505                 510

Ile Thr Ala Ala Thr Arg Val Gly Leu Gly Glu Ser Ser Val Trp Thr
        515                 520                 525

Ser His Arg Thr Pro Lys Ala Thr Ser Val Lys Ala Pro Lys Ser Pro
    530                 535                 540

Glu Leu His Leu Glu Pro Leu Asn Cys Thr Thr Ile Ser Val Arg Trp
545                 550                 555                 560

Gln Gln Asp Val Glu Asp Thr Ala Ala Ile Gln Gly Tyr Lys Leu Tyr
                565                 570                 575

Tyr Lys Glu Glu Gly Gln Gln Glu Asn Gly Pro Ile Phe Leu Asp Thr
            580                 585                 590

Lys Asp Leu Leu Tyr Thr Leu Ser Gly Leu Asp Pro Arg Arg Lys Tyr
        595                 600                 605

His Val Arg Leu Leu Ala Tyr Asn Asn Ile Asp Asp Gly Tyr Gln Ala
    610                 615                 620

Asp Gln Thr Val Ser Thr Pro Gly Cys Val Ser Val Arg Asp Arg Met
625                 630                 635                 640

Val Pro Pro Pro Pro Pro Pro His His Leu Tyr Ala Lys Ala Asn Thr
                645                 650                 655

Ser Ser Ser Ile Phe Leu His Trp Arg Arg Pro Ala Phe Thr Ala Ala
            660                 665                 670

Gln Ile Ile Asn Tyr Thr Ile Arg Cys Asn Pro Val Gly Leu Gln Asn
        675                 680                 685

Ala Ser Leu Val Leu Tyr Leu Gln Thr Ser Glu Thr His Met Leu Val
    690                 695                 700

Gln Gly Leu Glu Pro Asn Thr Lys Tyr Glu Phe Ala Val Arg Leu His
705                 710                 715                 720

Val Asp Gln Leu Ser Ser Pro Trp Ser Pro Val Val Tyr His Ser Thr
                725                 730                 735

Leu Pro Glu Ala Pro Ala Gly Pro Pro Val Gly Val Lys Val Thr Leu
            740                 745                 750

Ile Glu Asp Asp Thr Ala Leu Val Ser Trp Lys Pro Pro Asp Gly Pro
        755                 760                 765

Glu Thr Val Val Thr Arg Tyr Thr Ile Leu Tyr Ala Ser Arg Lys Ala
    770                 775                 780

Trp Ile Ala Gly Glu Trp Gln Val Leu His Arg Glu Gly Ala Ile Thr
785                 790                 795                 800

Met Ala Leu Leu Glu Asn Leu Val Ala Gly Asn Val Tyr Ile Val Lys
                805                 810                 815

Ile Ser Ala Ser Asn Glu Val Gly Glu Gly Pro Phe Ser Asn Ser Val
            820                 825                 830
```

```
Glu Leu Ala Val Leu Pro Lys Glu Thr Ser Glu Ser Asn Gln Arg Pro
        835                 840                 845

Lys Arg Leu Asp Ser Ala Asp Ala Lys Val Tyr Ser Gly Tyr Tyr His
    850                 855                 860

Leu Asp Gln Lys Ser Met Thr Gly Ile Ala Val Gly Val Gly Ile Ala
865                 870                 875                 880

Leu Thr Cys Ile Leu Ile Cys Val Leu Ile Leu Ile Tyr Arg Ser Lys
                885                 890                 895

Ala Arg Lys Ser Ser Ala Ser Lys Thr Ala Gln Asn Gly Thr Gln Gln
            900                 905                 910

Leu Pro Arg Thr Ser Ala Ser Leu Ala Ser Gly Asn Glu Val Gly Lys
        915                 920                 925

Asn Leu Glu Gly Ala Val Gly Asn Glu Glu Ser Leu Met Pro Met Ile
    930                 935                 940

Met Pro Asn Ser Phe Ile Asp Ala Lys Gly Gly Thr Asp Leu Ile Ile
945                 950                 955                 960

Asn Ser Tyr Gly Pro Ile Ile Lys Asn Asn Ser Lys Lys Lys Trp Phe
                965                 970                 975

Phe Phe Gln Asp Ser Lys Lys Ile Gln Val Glu Gln Pro Gln Arg Arg
            980                 985                 990

Phe Thr Pro Ala Val Cys Phe Tyr Gln Pro Gly Thr Thr Val Leu Ile
        995                 1000                1005

Ser Asp Glu Asp Ser Pro Ser Ser Pro Gly Gln Thr Thr Ser Phe Ser
    1010                1015                1020

Arg Pro Phe Gly Val Ala Ala Asp Thr Glu His Ser Ala Asn Ser Glu
1025                1030                1035                1040

Gly Ser His Glu Thr Gly Asp Ser Gly Arg Phe Ser His Glu Ser Asn
                1045                1050                1055

Asp Glu Ile His Leu Ser Ser Val Ile Ser Thr Thr Pro Pro Asn Leu
            1060                1065                1070
```

<210> SEQ ID NO 19
<211> LENGTH: 2724
<212> TYPE: DNA
<213> ORGANISM: homo sapiens

<400> SEQUENCE: 19

```
atgtctgaaa ataaacggat cgaggttctt tctaacggct ctttatacat cagtgaggtg      60

gaaggcaggc gaggagagca gtccgatgaa ggattttatc agtgcttggc aatgaacaaa     120

tatggagcca ttcttagtca aaaagctcat cttgccttat caactatttc tgcatttgaa     180

gtccagccaa tttccactga ggtccacgaa ggtggagttg ctcgatttgc atgcaagatt     240

tcatcccacc ctcctgcagt cataacatgg gagttcaatc ggacaactct acctatgact     300

atggacagga taactgccct accaacagga gtattgcaga tctatgatgt cagccaaagg     360

gattctggaa attatcgttg tattgctgcc actgtagccc accgacgtaa aagtatggag     420

gcctcgctaa ctgtgattcc agctaaggag tcaaaatcct tccacacacc arcaattata     480

gcaggtccac agaacataac aacatctctt catcagactg tagttttgga atgcatggcc     540

acaggaaatc ccaaaccaat catttcttgg agccgccttg atcacaaatc cattgatgtc     600

tttaatactc gggtacttgg aaatggtaat ctcatgatat ctgatgtcag gctacaacat     660

gctggagtat atgtttgtcg ggccactacc cctggcacac gcaactttac agttgctatg     720

gcaactttaa ctgtattagc tcctccttca tttgttgaat ggccagaaag tttaacaagg     780
```

-continued

```
cctcgagctg gcactgctcg atttgtgtgt caggcagaag gaatcccctc tcccaagatg    840

tcatggttga aaaatggaag gaagatacat tcgaatggta gaattaaaat gtacaacagt    900

aaattggtaa ttaaccagat tattcctgaa gatgatgcta tttatcagtg catggctgag    960

aatagccaag gatctatttt atctagagcc agactgactg tagtgatgtc agaagacaga   1020

cccagtgctc cctataatgt acatgctgaa accatgtcaa gctcagccat tcttttagcc   1080

tgggagaggc cactttataa ttcagacaaa gtcattgcct attctgtaca ctacatgaaa   1140

gcagaaggtt taaataatga agagtatcaa gtagtcatcg gaaatgacac aactcattat   1200

attattgatg acttagagcc tgccagcaat tatactttct acattgtagc atatatgcca   1260

atgggagcca gccagatgtc tgaccatgtg acacagaata ctctagagga tgaccccaga   1320

agaaaatatc atgtgagact cctggcttac aacaacatag acgatggcta tcaggcagat   1380

cagactgtca gcactccagg atgcgtgtct gttcgtgatc gcatggtccc tcctccacca   1440

ccaccccacc atctctatgc gaaggctaac acctcatctt ccatcttcct gcactggagg   1500

aggcctgcat tcaccgctgc acaaatcatt aactacacca tccgctgtaa tcctgttggc   1560

ctgcagaatg cttctttggt tctgtacctt caaacatcag aaactcacat gttggttcaa   1620

ggtctagaac caaacaccaa atacgaattt gccgttcgat tacatgtgga tcagctttcc   1680

agtccttgga gccctgtagt ctaccattct actcttccag aagcaccagc aggcccacca   1740

gttggagtaa aagtgacatt aatagaggat gacactgccc tggtttcttg gaaacccct   1800

gatggcccag aaacagttgt gacccgctat actatcttat atgcatctag gaaggcctgg   1860

attgcaggag agtggcaggt cttacaccgt gaaggggcaa taaccatggc tttgctagaa   1920

aacttggtag caggaaatgt gtacattgtc aagatatctg catccaatga ggtgggagaa   1980

ggaccctttt caaattctgt ggagctggca gtacttccaa aggaaacctc tgaatcaaat   2040

cagaggccca agcgtttaga ttctgctgat gccaaagttt attcaggata ttaccatctg   2100

gaccaaaaat caatgactgg cattgctgta ggtgttggca tagccttgac ctgcatcctc   2160

atctgtgttc tcatcttgat ataccgaagt aaagccagga aatcatctgc ttccaagacg   2220

gcacagaatg gaactcaaca gttacctcgt accagtgcct ccttagctag tggaaatgag   2280

gtaggaaaga acctggaagg agctgtagga aatgaagaat ctttaatgcc aatgatcatg   2340

ccaaacagct tcattgatgc aaagggagga actgacctga taattaatag ctatggtcct   2400

ataattaaaa acaactctaa gaaaaagtgg ttttttttcc aagactcaaa gaagatacaa   2460

gttgagcagc ctcaaagaag atttactcca gcggtctgct tttaccagcc aggcaccact   2520

gtattaatca gtgatgaaga ctcccctagc tccccaggtc agacaaccag cttctcaaga   2580

ccctttggtg ttgcagctga tacagaacat tcagcaaata gtgaaggcag ccatgagact   2640

ggggattctg gcggttttc tcatgagtcc aacgatgaga tacatctgtc ctcagttata   2700

agtaccacac cccccaacct ctga                                          2724
```

<210> SEQ ID NO 20
<211> LENGTH: 907
<212> TYPE: PRT
<213> ORGANISM: homo sapiens

<400> SEQUENCE: 20

```
Met Ser Glu Asn Lys Arg Ile Glu Val Leu Ser Asn Gly Ser Leu Tyr
 1               5                  10                  15

Ile Ser Glu Val Glu Gly Arg Arg Gly Glu Gln Ser Asp Glu Gly Phe
```

-continued

```
            20                  25                  30

Tyr Gln Cys Leu Ala Met Asn Lys Tyr Gly Ala Ile Leu Ser Gln Lys
        35                  40                  45

Ala His Leu Ala Leu Ser Thr Ile Ser Ala Phe Glu Val Gln Pro Ile
    50                  55                  60

Ser Thr Glu Val His Glu Gly Gly Val Ala Arg Phe Ala Cys Lys Ile
65                  70                  75                  80

Ser Ser His Pro Pro Ala Val Ile Thr Trp Glu Phe Asn Arg Thr Thr
                85                  90                  95

Leu Pro Met Thr Met Asp Arg Ile Thr Ala Leu Pro Thr Gly Val Leu
            100                 105                 110

Gln Ile Tyr Asp Val Ser Gln Arg Asp Ser Gly Asn Tyr Arg Cys Ile
        115                 120                 125

Ala Ala Thr Val Ala His Arg Arg Lys Ser Met Glu Ala Ser Leu Thr
    130                 135                 140

Val Ile Pro Ala Lys Glu Ser Lys Ser Phe His Thr Pro Thr Ile Ile
145                 150                 155                 160

Ala Gly Pro Gln Asn Ile Thr Thr Ser Leu His Gln Thr Val Val Leu
                165                 170                 175

Glu Cys Met Ala Thr Gly Asn Pro Lys Pro Ile Ile Ser Trp Ser Arg
            180                 185                 190

Leu Asp His Lys Ser Ile Asp Val Phe Asn Thr Arg Val Leu Gly Asn
        195                 200                 205

Gly Asn Leu Met Ile Ser Asp Val Arg Leu Gln His Ala Gly Val Tyr
    210                 215                 220

Val Cys Arg Ala Thr Thr Pro Gly Thr Arg Asn Phe Thr Val Ala Met
225                 230                 235                 240

Ala Thr Leu Thr Val Leu Ala Pro Pro Ser Phe Val Glu Trp Pro Glu
                245                 250                 255

Ser Leu Thr Arg Pro Arg Ala Gly Thr Ala Arg Phe Val Cys Gln Ala
            260                 265                 270

Glu Gly Ile Pro Ser Pro Lys Met Ser Trp Leu Lys Asn Gly Arg Lys
        275                 280                 285

Ile His Ser Asn Gly Arg Ile Lys Met Tyr Asn Ser Lys Leu Val Ile
    290                 295                 300

Asn Gln Ile Ile Pro Glu Asp Asp Ala Ile Tyr Gln Cys Met Ala Glu
305                 310                 315                 320

Asn Ser Gln Gly Ser Ile Leu Ser Arg Ala Arg Leu Thr Val Val Met
                325                 330                 335

Ser Glu Asp Arg Pro Ser Ala Pro Tyr Asn Val His Ala Glu Thr Met
            340                 345                 350

Ser Ser Ser Ala Ile Leu Leu Ala Trp Glu Arg Pro Leu Tyr Asn Ser
        355                 360                 365

Asp Lys Val Ile Ala Tyr Ser Val His Tyr Met Lys Ala Glu Gly Leu
    370                 375                 380

Asn Asn Glu Glu Tyr Gln Val Val Ile Gly Asn Asp Thr Thr His Tyr
385                 390                 395                 400

Ile Ile Asp Asp Leu Glu Pro Ala Ser Asn Tyr Thr Phe Tyr Ile Val
                405                 410                 415

Ala Tyr Met Pro Met Gly Ala Ser Gln Met Ser Asp His Val Thr Gln
            420                 425                 430

Asn Thr Leu Glu Asp Asp Pro Arg Arg Lys Tyr His Val Arg Leu Leu
        435                 440                 445
```

-continued

```
Ala Tyr Asn Asn Ile Asp Asp Gly Tyr Gln Ala Asp Gln Thr Val Ser
    450                 455                 460

Thr Pro Gly Cys Val Ser Val Arg Asp Arg Met Val Pro Pro Pro Pro
465                 470                 475                 480

Pro Pro His His Leu Tyr Ala Lys Ala Asn Thr Ser Ser Ser Ile Phe
                485                 490                 495

Leu His Trp Arg Arg Pro Ala Phe Thr Ala Ala Gln Ile Ile Asn Tyr
            500                 505                 510

Thr Ile Arg Cys Asn Pro Val Gly Leu Gln Asn Ala Ser Leu Val Leu
        515                 520                 525

Tyr Leu Gln Thr Ser Glu Thr His Met Leu Val Gln Gly Leu Glu Pro
    530                 535                 540

Asn Thr Lys Tyr Glu Phe Ala Val Arg Leu His Val Asp Gln Leu Ser
545                 550                 555                 560

Ser Pro Trp Ser Pro Val Val Tyr His Ser Thr Leu Pro Glu Ala Pro
                565                 570                 575

Ala Gly Pro Pro Val Gly Val Lys Val Thr Leu Ile Glu Asp Asp Thr
            580                 585                 590

Ala Leu Val Ser Trp Lys Pro Pro Asp Gly Pro Glu Thr Val Val Thr
        595                 600                 605

Arg Tyr Thr Ile Leu Tyr Ala Ser Arg Lys Ala Trp Ile Ala Gly Glu
    610                 615                 620

Trp Gln Val Leu His Arg Glu Gly Ala Ile Thr Met Ala Leu Leu Glu
625                 630                 635                 640

Asn Leu Val Ala Gly Asn Val Tyr Ile Val Lys Ile Ser Ala Ser Asn
                645                 650                 655

Glu Val Gly Glu Gly Pro Phe Ser Asn Ser Val Glu Leu Ala Val Leu
            660                 665                 670

Pro Lys Glu Thr Ser Glu Ser Asn Gln Arg Pro Lys Arg Leu Asp Ser
        675                 680                 685

Ala Asp Ala Lys Val Tyr Ser Gly Tyr Tyr His Leu Asp Gln Lys Ser
    690                 695                 700

Met Thr Gly Ile Ala Val Gly Val Gly Ile Ala Leu Thr Cys Ile Leu
705                 710                 715                 720

Ile Cys Val Leu Ile Leu Ile Tyr Arg Ser Lys Ala Arg Lys Ser Ser
                725                 730                 735

Ala Ser Lys Thr Ala Gln Asn Gly Thr Gln Gln Leu Pro Arg Thr Ser
            740                 745                 750

Ala Ser Leu Ala Ser Gly Asn Glu Val Gly Lys Asn Leu Glu Gly Ala
        755                 760                 765

Val Gly Asn Glu Glu Ser Leu Met Pro Met Ile Met Pro Asn Ser Phe
    770                 775                 780

Ile Asp Ala Lys Gly Gly Thr Asp Leu Ile Ile Asn Ser Tyr Gly Pro
785                 790                 795                 800

Ile Ile Lys Asn Asn Ser Lys Lys Lys Trp Phe Phe Phe Gln Asp Ser
                805                 810                 815

Lys Lys Ile Gln Val Glu Gln Pro Gln Arg Arg Phe Thr Pro Ala Val
            820                 825                 830

Cys Phe Tyr Gln Pro Gly Thr Thr Val Leu Ile Ser Asp Glu Asp Ser
        835                 840                 845

Pro Ser Ser Pro Gly Gln Thr Thr Ser Phe Ser Arg Pro Phe Gly Val
    850                 855                 860
```

-continued

```
Ala Ala Asp Thr Glu His Ser Ala Asn Ser Glu Gly Ser His Glu Thr
865                 870                 875                 880

Gly Asp Ser Gly Arg Phe Ser His Glu Ser Asn Asp Glu Ile His Leu
                885                 890                 895

Ser Ser Val Ile Ser Thr Thr Pro Pro Asn Leu
            900                 905


<210> SEQ ID NO 21
<211> LENGTH: 2139
<212> TYPE: DNA
<213> ORGANISM: homo sapiens

<400> SEQUENCE: 21

atgtcatggt tgaaaaatgg aaggaagata cattcgaatg gtagaattaa aatgtacaac     60

agtaaattgg taattaacca gattattcct gaagatgatg ctatttatca gtgcatggct    120

gagaatagcc aaggatctat tttatctaga gccagactga ctgtagtgat gtcagaagac    180

agacccagtg ctccctataa tgtacatgct gaaaccatgt caagctcagc cattctttta    240

gcctgggaga ggccacttta taattcagac aaagtcattg cctattctgt acactacatg    300

aaagcagaag gtttaaataa tgaagagtat caagtagtca tcggaaatga cacaactcat    360

tatattattg atgacttaga gcctgccagc aattatactt tctacattgt agcatatatg    420

ccaatgggag ccagccagat gtctgaccat gtgacacaga atactctaga ggatgttccc    480

ctgagacctc ctgaaattag tttgacaagt cgaagtccca ctgatattct catctcctgg    540

ctgccaatcc cagccaaata tcggcggggc caagtggtgc tgtatcgctt gtctttccgc    600

ctaagtactg agaattcaat ccaagttctg gagctcccgg ggaccacgca tgagtacctt    660

ttggaaggcc tgaaacctga cagtgtctac ctggttcgga ttactgctgc caccagagtg    720

gggctgggag agtcatcagt atggacttca cataggacgc ccaaagctac aagcgtgaaa    780

gcccctaagt ctccagagtt gcatttggag cctctgaact gtaccaccat ttctgtgagg    840

tggcagcaag atgtagagga cacagctgct attcagggct acaagctgta ctacaaggaa    900

gaagggcagc aggagaatgg gcccattttc ttggatacca aggacctact ctatactctc    960

agtggcttag accccagaag aaaatatcat gtgagactcc tggcttacaa caacatagac   1020

gatggctatc aggcagatca gactgtcagc actccaggat gcgtgtctgt tcgtgatcgc   1080

atggtccctc ctccaccacc accccaccat ctctatgcga aggctaacac ctcatcttcc   1140

atcttcctgc actggaggag gcctgcattc accgctgcac aaatcattaa ctacaccatc   1200

cgctgtaatc ctgttggcct gcagaatgct tctttggttc tgtaccttca aacatcagaa   1260

actcacatgt tggttcaagg tctagaacca aacaccaaat acgaatttgc cgttcgatta   1320

catgtggatc agctttccag tccttggagc cctgtagtct accattctac tcttccagaa   1380

gcaccagcag gcccaccagt tggagtaaaa gtgacattaa tagaggatga cactgccctg   1440

gtttcttgga aacccccctga tggcccagaa acagttgtga cccgctatac tatcttatat   1500

gcatctagga aggcctggat tgcaggagag tggcaggtct tacaccgtga aggggcaata   1560

accatggctt tgctagaaaa cttggtagca ggaaatgtgt acattgtcaa gatatctgca   1620

tccaatgagg tgggagaagg acccttttca aattctgtgg agctggcagt acttccaaag   1680

gaaacctctg aatcaaatca gaggcccaag cgtttagatt ctgctgatgc caaagtttat   1740

tcaggatatt accatctgga ccaaaaatca atgactggca ttgctgtagg tgttggcata   1800

gccttgacct gcatcctcat ctgtgttctc atcttgatat accgaagtaa agccaggaaa   1860
```

-continued

```
tcatctgctt ccaagacggc acagaatgga actcaacagt tacctcgtac cagtgcctcc   1920

ttagctagtg gaaatgaggt aggaaagaac ctggaaggag ctgtaggaaa tgaagaatct   1980

ttaatgccaa tgatcatgcc aaacagcttc attgatgcaa aggtactgag ctgcgggatt   2040

tgctgcataa gccgttcttc cattcctcct ccctgtgtgt gtaaaatgta cttcccccaa   2100

aattgtatgt tgaatgtatt ataccaatac tcttattaa                          2139
```

<210> SEQ ID NO 22
<211> LENGTH: 712
<212> TYPE: PRT
<213> ORGANISM: homo sapiens

<400> SEQUENCE: 22

```
Met Ser Trp Leu Lys Asn Gly Arg Lys Ile His Ser Asn Gly Arg Ile
 1               5                  10                  15

Lys Met Tyr Asn Ser Lys Leu Val Ile Asn Gln Ile Ile Pro Glu Asp
            20                  25                  30

Asp Ala Ile Tyr Gln Cys Met Ala Glu Asn Ser Gln Gly Ser Ile Leu
        35                  40                  45

Ser Arg Ala Arg Leu Thr Val Val Met Ser Glu Asp Arg Pro Ser Ala
    50                  55                  60

Pro Tyr Asn Val His Ala Glu Thr Met Ser Ser Ser Ala Ile Leu Leu
65                  70                  75                  80

Ala Trp Glu Arg Pro Leu Tyr Asn Ser Asp Lys Val Ile Ala Tyr Ser
                85                  90                  95

Val His Tyr Met Lys Ala Glu Gly Leu Asn Asn Glu Glu Tyr Gln Val
            100                 105                 110

Val Ile Gly Asn Asp Thr Thr His Tyr Ile Ile Asp Asp Leu Glu Pro
        115                 120                 125

Ala Ser Asn Tyr Thr Phe Tyr Ile Val Ala Tyr Met Pro Met Gly Ala
    130                 135                 140

Ser Gln Met Ser Asp His Val Thr Gln Asn Thr Leu Glu Asp Val Pro
145                 150                 155                 160

Leu Arg Pro Pro Glu Ile Ser Leu Thr Ser Arg Ser Pro Thr Asp Ile
                165                 170                 175

Leu Ile Ser Trp Leu Pro Ile Pro Ala Lys Tyr Arg Arg Gly Gln Val
            180                 185                 190

Val Leu Tyr Arg Leu Ser Phe Arg Leu Ser Thr Glu Asn Ser Ile Gln
        195                 200                 205

Val Leu Glu Leu Pro Gly Thr Thr His Glu Tyr Leu Leu Glu Gly Leu
    210                 215                 220

Lys Pro Asp Ser Val Tyr Leu Val Arg Ile Thr Ala Ala Thr Arg Val
225                 230                 235                 240

Gly Leu Gly Glu Ser Ser Val Trp Thr Ser His Arg Thr Pro Lys Ala
                245                 250                 255

Thr Ser Val Lys Ala Pro Lys Ser Pro Glu Leu His Leu Glu Pro Leu
            260                 265                 270

Asn Cys Thr Thr Ile Ser Val Arg Trp Gln Gln Asp Val Glu Asp Thr
        275                 280                 285

Ala Ala Ile Gln Gly Tyr Lys Leu Tyr Tyr Lys Glu Glu Gly Gln Gln
    290                 295                 300

Glu Asn Gly Pro Ile Phe Leu Asp Thr Lys Asp Leu Leu Tyr Thr Leu
305                 310                 315                 320

Ser Gly Leu Asp Pro Arg Arg Lys Tyr His Val Arg Leu Leu Ala Tyr
```

-continued

```
                325                 330                 335

Asn Asn Ile Asp Asp Gly Tyr Gln Ala Asp Gln Thr Val Ser Thr Pro
            340                 345                 350

Gly Cys Val Ser Val Arg Asp Arg Met Val Pro Pro Pro Pro Pro Pro
        355                 360                 365

His His Leu Tyr Ala Lys Ala Asn Thr Ser Ser Ser Ile Phe Leu His
    370                 375                 380

Trp Arg Arg Pro Ala Phe Thr Ala Ala Gln Ile Ile Asn Tyr Thr Ile
385                 390                 395                 400

Arg Cys Asn Pro Val Gly Leu Gln Asn Ala Ser Leu Val Leu Tyr Leu
                405                 410                 415

Gln Thr Ser Glu Thr His Met Leu Val Gln Gly Leu Glu Pro Asn Thr
            420                 425                 430

Lys Tyr Glu Phe Ala Val Arg Leu His Val Asp Gln Leu Ser Ser Pro
        435                 440                 445

Trp Ser Pro Val Val Tyr His Ser Thr Leu Pro Glu Ala Pro Ala Gly
    450                 455                 460

Pro Pro Val Gly Val Lys Val Thr Leu Ile Glu Asp Asp Thr Ala Leu
465                 470                 475                 480

Val Ser Trp Lys Pro Pro Asp Gly Pro Glu Thr Val Val Thr Arg Tyr
                485                 490                 495

Thr Ile Leu Tyr Ala Ser Arg Lys Ala Trp Ile Ala Gly Glu Trp Gln
            500                 505                 510

Val Leu His Arg Glu Gly Ala Ile Thr Met Ala Leu Leu Glu Asn Leu
        515                 520                 525

Val Ala Gly Asn Val Tyr Ile Val Lys Ile Ser Ala Ser Asn Glu Val
    530                 535                 540

Gly Glu Gly Pro Phe Ser Asn Ser Val Glu Leu Ala Val Leu Pro Lys
545                 550                 555                 560

Glu Thr Ser Glu Ser Asn Gln Arg Pro Lys Arg Leu Asp Ser Ala Asp
                565                 570                 575

Ala Lys Val Tyr Ser Gly Tyr Tyr His Leu Asp Gln Lys Ser Met Thr
            580                 585                 590

Gly Ile Ala Val Gly Val Gly Ile Ala Leu Thr Cys Ile Leu Ile Cys
        595                 600                 605

Val Leu Ile Leu Ile Tyr Arg Ser Lys Ala Arg Lys Ser Ser Ala Ser
    610                 615                 620

Lys Thr Ala Gln Asn Gly Thr Gln Gln Leu Pro Arg Thr Ser Ala Ser
625                 630                 635                 640

Leu Ala Ser Gly Asn Glu Val Gly Lys Asn Leu Glu Gly Ala Val Gly
                645                 650                 655

Asn Glu Glu Ser Leu Met Pro Met Ile Met Pro Asn Ser Phe Ile Asp
            660                 665                 670

Ala Lys Val Leu Ser Cys Gly Ile Cys Cys Ile Ser Arg Ser Ser Ile
        675                 680                 685

Pro Pro Pro Cys Val Cys Lys Met Tyr Phe Pro Gln Asn Cys Met Leu
    690                 695                 700

Asn Val Leu Tyr Gln Tyr Ser Tyr
705                 710


<210> SEQ ID NO 23
<211> LENGTH: 1875
<212> TYPE: DNA
<213> ORGANISM: homo sapiens
```

<400> SEQUENCE: 23

```
atggaaggaa gatacattcg aatggtagaa ttaaaatgta caacaggttt aaataatgaa     60
gagtatcaag tagtcatcgg aaatgacaca actcattata ttattgatga cttagagcct    120
gccagcaatt atactttcta cattgtagca tatatgccaa tgggagccag ccagatgtct    180
gaccatgtga cacagaatac tctagaggat gttcccctga gacctcctga aattagtttg    240
acaagtcgaa gtcccactga tattctcatc tcctggctgc caatcccagc caaatatcgg    300
cggggccaag tggtgctgta tcgcttgtct ttccgcctaa gtactgagaa ttcaatccaa    360
gttctggagc tcccggggac cacgcatgag taccttttgg aaggcctgaa acctgacagt    420
gtctacctgg ttcggattac tgctgccacc agagtggggc tgggagagtc atcagtatgg    480
acttcacata ggacgcccaa agctacaagc gtgaaagccc ctaagtctcc agagttgcat    540
ttggagcctc tgaactgtac caccatttct gtgaggtggc agcaagatgt agaggacaca    600
gctgctattc agggctacaa gctgtactac aaggaagaag ggcagcagga gaatgggccc    660
attttcttgg ataccaagga cctactctat actctcagtg gcttagaccc cagaagaaaa    720
tatcatgtga gactcctggc ttacaacaac atagacgatg gctatcaggc agatcagact    780
gtcagcactc caggatgcgt gtctgttcgt gatcgcatgg tccctcctcc accaccaccc    840
caccatctct atgcgaaggc taacacctca tcttccatct tcctgcactg gaggaggcct    900
gcattcaccg ctgcacaaat cattaactac accatccgct gtaatcctgt tggcctgcag    960
aatgcttctt tggttctgta ccttcaaaca tcagaaactc acatgttggt tcaaggtcta   1020
gaaccaaaca ccaaatacga atttgccgtt cgattacatg tggatcagct ttccagtcct   1080
tggagccctg tagtctacca ttctactctt ccagaagcac cagcaggccc accagttgga   1140
gtaaaagtga cattaataga ggatgacact gccctggttt cttggaaacc ccctgatggc   1200
ccagaaacag ttgtgacccg ctatactatc ttatatgcat ctaggaaggc ctggattgca   1260
ggagagtggc aggtcttaca ccgtgaaggg gcaataacca tggctttgct agaaaacttg   1320
gtagcaggaa atgtgtacat tgtcaagata tctgcatcca atgaggtggg agaaggaccc   1380
ttttcaaatt ctgtggagct ggcagtactt ccaaaggaaa cctctgaatc aaatcagagg   1440
cccaagcgtt tagattctgc tgatgccaaa gtttattcag gatattacca tctggaccaa   1500
aaatcaatga ctggcattgc tgtaggtgtt ggcatagcct tgacctgcat cctcatctgt   1560
gttctcatct tgatataccg aagtaaagcc aggaaatcat ctgcttccaa gacggcacag   1620
aatggaactc aacagttacc tcgtaccagt gcctccttag ctagtggaaa tgaggtagga   1680
aagaacctgg aaggagctgt aggaaatgaa gaatctttaa tgccaatgat catgccaaac   1740
agcttcattg atgcaaaggt actgagctgc gggatttgct gcataagccg ttcttccatt   1800
cctcctccct gtgtgtgtaa aatgtacttc ccccaaaatt gtatgttgaa tgtattatac   1860
caatactctt attaa                                                    1875
```

<210> SEQ ID NO 24
<211> LENGTH: 624
<212> TYPE: PRT
<213> ORGANISM: homo sapiens

<400> SEQUENCE: 24

```
Met Glu Gly Arg Tyr Ile Arg Met Val Glu Leu Lys Cys Thr Thr Gly
 1               5                  10                  15

Leu Asn Asn Glu Glu Tyr Gln Val Val Ile Gly Asn Asp Thr Thr His
```

-continued

```
            20                  25                  30

Tyr Ile Ile Asp Asp Leu Glu Pro Ala Ser Asn Tyr Thr Phe Tyr Ile
        35                  40                  45

Val Ala Tyr Met Pro Met Gly Ala Ser Gln Met Ser Asp His Val Thr
    50                  55                  60

Gln Asn Thr Leu Glu Asp Val Pro Leu Arg Pro Pro Glu Ile Ser Leu
65                  70                  75                  80

Thr Ser Arg Ser Pro Thr Asp Ile Leu Ile Ser Trp Leu Pro Ile Pro
                85                  90                  95

Ala Lys Tyr Arg Arg Gly Gln Val Val Leu Tyr Arg Leu Ser Phe Arg
            100                 105                 110

Leu Ser Thr Glu Asn Ser Ile Gln Val Leu Glu Leu Pro Gly Thr Thr
        115                 120                 125

His Glu Tyr Leu Leu Glu Gly Leu Lys Pro Asp Ser Val Tyr Leu Val
    130                 135                 140

Arg Ile Thr Ala Ala Thr Arg Val Gly Leu Gly Glu Ser Ser Val Trp
145                 150                 155                 160

Thr Ser His Arg Thr Pro Lys Ala Thr Ser Val Lys Ala Pro Lys Ser
                165                 170                 175

Pro Glu Leu His Leu Glu Pro Leu Asn Cys Thr Thr Ile Ser Val Arg
            180                 185                 190

Trp Gln Gln Asp Val Glu Asp Thr Ala Ala Ile Gln Gly Tyr Lys Leu
        195                 200                 205

Tyr Tyr Lys Glu Glu Gly Gln Gln Glu Asn Gly Pro Ile Phe Leu Asp
    210                 215                 220

Thr Lys Asp Leu Leu Tyr Thr Leu Ser Gly Leu Asp Pro Arg Arg Lys
225                 230                 235                 240

Tyr His Val Arg Leu Leu Ala Tyr Asn Asn Ile Asp Asp Gly Tyr Gln
                245                 250                 255

Ala Asp Gln Thr Val Ser Thr Pro Gly Cys Val Ser Val Arg Asp Arg
            260                 265                 270

Met Val Pro Pro Pro Pro Pro Pro His His Leu Tyr Ala Lys Ala Asn
        275                 280                 285

Thr Ser Ser Ser Ile Phe Leu His Trp Arg Arg Pro Ala Phe Thr Ala
    290                 295                 300

Ala Gln Ile Ile Asn Tyr Thr Ile Arg Cys Asn Pro Val Gly Leu Gln
305                 310                 315                 320

Asn Ala Ser Leu Val Leu Tyr Leu Gln Thr Ser Glu Thr His Met Leu
                325                 330                 335

Val Gln Gly Leu Glu Pro Asn Thr Lys Tyr Glu Phe Ala Val Arg Leu
            340                 345                 350

His Val Asp Gln Leu Ser Ser Pro Trp Ser Pro Val Val Tyr His Ser
        355                 360                 365

Thr Leu Pro Glu Ala Pro Ala Gly Pro Pro Val Gly Val Lys Val Thr
    370                 375                 380

Leu Ile Glu Asp Asp Thr Ala Leu Val Ser Trp Lys Pro Pro Asp Gly
385                 390                 395                 400

Pro Glu Thr Val Val Thr Arg Tyr Thr Ile Leu Tyr Ala Ser Arg Lys
                405                 410                 415

Ala Trp Ile Ala Gly Glu Trp Gln Val Leu His Arg Glu Gly Ala Ile
            420                 425                 430

Thr Met Ala Leu Leu Glu Asn Leu Val Ala Gly Asn Val Tyr Ile Val
        435                 440                 445
```

-continued

```
Lys Ile Ser Ala Ser Asn Glu Val Gly Glu Gly Pro Phe Ser Asn Ser
    450                 455                 460

Val Glu Leu Ala Val Leu Pro Lys Glu Thr Ser Glu Ser Asn Gln Arg
465                 470                 475                 480

Pro Lys Arg Leu Asp Ser Ala Asp Ala Lys Val Tyr Ser Gly Tyr Tyr
                485                 490                 495

His Leu Asp Gln Lys Ser Met Thr Gly Ile Ala Val Gly Val Gly Ile
            500                 505                 510

Ala Leu Thr Cys Ile Leu Ile Cys Val Leu Ile Leu Ile Tyr Arg Ser
        515                 520                 525

Lys Ala Arg Lys Ser Ser Ala Ser Lys Thr Ala Gln Asn Gly Thr Gln
    530                 535                 540

Gln Leu Pro Arg Thr Ser Ala Ser Leu Ala Ser Gly Asn Glu Val Gly
545                 550                 555                 560

Lys Asn Leu Glu Gly Ala Val Gly Asn Glu Glu Ser Leu Met Pro Met
                565                 570                 575

Ile Met Pro Asn Ser Phe Ile Asp Ala Lys Val Leu Ser Cys Gly Ile
            580                 585                 590

Cys Cys Ile Ser Arg Ser Ser Ile Pro Pro Pro Cys Val Cys Lys Met
        595                 600                 605

Tyr Phe Pro Gln Asn Cys Met Leu Asn Val Leu Tyr Gln Tyr Ser Tyr
    610                 615                 620
```

<210> SEQ ID NO 25
<211> LENGTH: 1644
<212> TYPE: DNA
<213> ORGANISM: homo sapiens

<400> SEQUENCE: 25

```
atgtcatggt tgaaaaatgg aaggaagata cattcgaatg gtagaattaa aatgtacaac      60

agtaaattgg taattaacca gattattcct gaagatgatg ctatttatca gtgcatggct     120

gagaatagcc aaggatctat tttatctaga gccagactga ctgtagtgat gtcagaagac     180

agacccagtg ctccctataa tgtacatgct gaaaccatgt caagctcagc cattctttta     240

gcctgggaga ggccacttta taattcagac aaagtcattg cctattctgt acactacatg     300

aaagcagaag gtttaaataa tgaagagtat caagtagtca tcggaaatga cacaactcat     360

tatattattg atgacttaga gcctgccagc aattatactt tctacattgt agcatatatg     420

ccaatgggag ccagccagat gtctgaccat gtgacacaga atactctaga ggatgacccc     480

agaagaaaat atcatgtgag actcctggct tacaacaaca tagacgatgg ctatcaggca     540

gatcagactg tcagcactcc aggatgcgtg tctgttcgtg atcgcatggt ccctcctcca     600

ccaccacccc accatctcta tgcgaaggct aacacctcat cttccatctt cctgcactgg     660

aggaggcctg cattcaccgc tgcacaaatc attaactaca ccatccgctg taatcctgtt     720

ggcctgcaga atgcttcttt ggttctgtac cttcaaacat cagaaactca catgttggtt     780

caaggtctag aaccaaacac caaatacgaa tttgccgttc gattacatgt ggatcagctt     840

tccagtcctt ggagccctgt agtctaccat tctactcttc cagaagcacc agcaggccca     900

ccagttggag taaaagtgac attaatagag gatgacactg ccctggtttc ttggaaaccc     960

cctgatggcc cagaaacagt tgtgacccgc tatactatct tatatgcatc taggaaggcc    1020

tggattgcag gagagtggca ggtcttacac cgtgaagggg caataaccat ggctttgcta    1080

gaaaacttgg tagcaggaaa tgtgtacatt gtcaagatat ctgcatccaa tgaggtggga    1140
```

```
gaaggaccct tttcaaattc tgtggagctg gcagtacttc caaaggaaac ctctgaatca   1200

aatcagaggc ccaagcgttt agattctgct gatgccaaag tttattcagg atattaccat   1260

ctggaccaaa aatcaatgac tggcattgct gtaggtgttg gcatagcctt gacctgcatc   1320

ctcatctgtg ttctcatctt gatataccga agtaaagcca ggaaatcatc tgcttccaag   1380

acggcacaga atggaactca acagttacct cgtaccagtg cctccttagc tagtggaaat   1440

gaggtaggaa agaacctgga aggagctgta ggaaatgaag aatctttaat gccaatgatc   1500

atgccaaaca gcttcattga tgcaaaggta ctgagctgcg ggatttgctg cataagccgt   1560

tcttccattc ctcctccctg tgtgtgtaaa atgtacttcc cccaaaattg tatgttgaat   1620

gtattatacc aatactctta ttaa                                          1644
```

<210> SEQ ID NO 26
<211> LENGTH: 547
<212> TYPE: PRT
<213> ORGANISM: homo sapiens

<400> SEQUENCE: 26

```
Met Ser Trp Leu Lys Asn Gly Arg Lys Ile His Ser Asn Gly Arg Ile
 1               5                  10                  15

Lys Met Tyr Asn Ser Lys Leu Val Ile Asn Gln Ile Ile Pro Glu Asp
            20                  25                  30

Asp Ala Ile Tyr Gln Cys Met Ala Glu Asn Ser Gln Gly Ser Ile Leu
        35                  40                  45

Ser Arg Ala Arg Leu Thr Val Val Met Ser Glu Asp Arg Pro Ser Ala
    50                  55                  60

Pro Tyr Asn Val His Ala Glu Thr Met Ser Ser Ser Ala Ile Leu Leu
65                  70                  75                  80

Ala Trp Glu Arg Pro Leu Tyr Asn Ser Asp Lys Val Ile Ala Tyr Ser
                85                  90                  95

Val His Tyr Met Lys Ala Glu Gly Leu Asn Asn Glu Glu Tyr Gln Val
            100                 105                 110

Val Ile Gly Asn Asp Thr Thr His Tyr Ile Ile Asp Asp Leu Glu Pro
        115                 120                 125

Ala Ser Asn Tyr Thr Phe Tyr Ile Val Ala Tyr Met Pro Met Gly Ala
    130                 135                 140

Ser Gln Met Ser Asp His Val Thr Gln Asn Thr Leu Glu Asp Asp Pro
145                 150                 155                 160

Arg Arg Lys Tyr His Val Arg Leu Leu Ala Tyr Asn Asn Ile Asp Asp
                165                 170                 175

Gly Tyr Gln Ala Asp Gln Thr Val Ser Thr Pro Gly Cys Val Ser Val
            180                 185                 190

Arg Asp Arg Met Val Pro Pro Pro Pro Pro Pro His His Leu Tyr Ala
        195                 200                 205

Lys Ala Asn Thr Ser Ser Ser Ile Phe Leu His Trp Arg Arg Pro Ala
    210                 215                 220

Phe Thr Ala Ala Gln Ile Ile Asn Tyr Thr Ile Arg Cys Asn Pro Val
225                 230                 235                 240

Gly Leu Gln Asn Ala Ser Leu Val Leu Tyr Leu Gln Thr Ser Glu Thr
                245                 250                 255

His Met Leu Val Gln Gly Leu Glu Pro Asn Thr Lys Tyr Glu Phe Ala
            260                 265                 270

Val Arg Leu His Val Asp Gln Leu Ser Ser Pro Trp Ser Pro Val Val
```

-continued

```
        275                 280                 285

Tyr His Ser Thr Leu Pro Glu Ala Pro Ala Gly Pro Pro Val Gly Val
    290                 295                 300

Lys Val Thr Leu Ile Glu Asp Asp Thr Ala Leu Val Ser Trp Lys Pro
305                 310                 315                 320

Pro Asp Gly Pro Glu Thr Val Val Thr Arg Tyr Thr Ile Leu Tyr Ala
                325                 330                 335

Ser Arg Lys Ala Trp Ile Ala Gly Glu Trp Gln Val Leu His Arg Glu
            340                 345                 350

Gly Ala Ile Thr Met Ala Leu Leu Glu Asn Leu Val Ala Gly Asn Val
        355                 360                 365

Tyr Ile Val Lys Ile Ser Ala Ser Asn Glu Val Gly Glu Gly Pro Phe
    370                 375                 380

Ser Asn Ser Val Glu Leu Ala Val Leu Pro Lys Glu Thr Ser Glu Ser
385                 390                 395                 400

Asn Gln Arg Pro Lys Arg Leu Asp Ser Ala Asp Ala Lys Val Tyr Ser
                405                 410                 415

Gly Tyr Tyr His Leu Asp Gln Lys Ser Met Thr Gly Ile Ala Val Gly
            420                 425                 430

Val Gly Ile Ala Leu Thr Cys Ile Leu Ile Cys Val Leu Ile Leu Ile
        435                 440                 445

Tyr Arg Ser Lys Ala Arg Lys Ser Ser Ala Ser Lys Thr Ala Gln Asn
    450                 455                 460

Gly Thr Gln Gln Leu Pro Arg Thr Ser Ala Ser Leu Ala Ser Gly Asn
465                 470                 475                 480

Glu Val Gly Lys Asn Leu Glu Gly Ala Val Gly Asn Glu Glu Ser Leu
                485                 490                 495

Met Pro Met Ile Met Pro Asn Ser Phe Ile Asp Ala Lys Val Leu Ser
            500                 505                 510

Cys Gly Ile Cys Cys Ile Ser Arg Ser Ser Ile Pro Pro Pro Cys Val
        515                 520                 525

Cys Lys Met Tyr Phe Pro Gln Asn Cys Met Leu Asn Val Leu Tyr Gln
    530                 535                 540

Tyr Ser Tyr
545


<210> SEQ ID NO 27
<211> LENGTH: 2382
<212> TYPE: DNA
<213> ORGANISM: homo sapiens

<400> SEQUENCE: 27

atgtcatggt tgaaaaatgg aaggaagata cattcgaatg gtagaattaa aatgtacaac     60

agtaaattgg taattaacca gattattcct gaagatgatg ctatttatca gtgcatggct    120

gagaatagcc aaggatctat tttatctaga gccagactga ctgtagtgat gtcagaagac    180

agacccagtg ctccctataa tgtacatgct gaaaccatgt caagctcagc cattctttta    240

gcctgggaga ggccacttta taattcagac aaagtcattg cctattctgt acactacatg    300

aaagcagaag gtttaaataa tgaagagtat caagtagtca tcggaaatga cacaactcat    360

tatattattg atgacttaga gcctgccagc aattatactt tctacattgt agcatatatg    420

ccaatgggag ccagccagat gtctgaccat gtgacacaga atactctaga ggatgttccc    480

ctgagacctc ctgaaattag tttgacaagt cgaagtccca ctgatattct catctcctgg    540
```

-continued

```
ctgccaatcc cagccaaata tcggcggggc caagtggtgc tgtatcgctt gtctttccgc    600

ctaagtactg agaattcaat ccaagttctg gagctcccgg ggaccacgca tgagtacctt    660

ttggaaggcc tgaaacctga cagtgtctac ctggttcgga ttactgctgc caccagagtg    720

gggctgggag agtcatcagt atggacttca cataggacgc ccaaagctac aagcgtgaaa    780

gcccctaagt ctccagagtt gcatttggag cctctgaact gtaccaccat ttctgtgagg    840

tggcagcaag atgtagagga cacagctgct attcagggct acaagctgta ctacaaggaa    900

gaagggcagc aggagaatgg gcccattttc ttggatacca aggacctact ctatactctc    960

agtggcttag accccagaag aaaatatcat gtgagactcc tggcttacaa caacatagac   1020

gatggctatc aggcagatca gactgtcagc actccaggat gcgtgtctgt tcgtgatcgc   1080

atggtccctc ctccaccacc accccaccat ctctatgcga aggctaacac ctcatcttcc   1140

atcttcctgc actggaggag gcctgcattc accgctgcac aaatcattaa ctacaccatc   1200

cgctgtaatc ctgttggcct gcagaatgct tctttggttc tgtaccttca aacatcagaa   1260

actcacatgt tggttcaagg tctagaacca aacaccaaat acgaatttgc cgttcgatta   1320

catgtggatc agctttccag tccttggagc cctgtagtct accattctac tcttccagaa   1380

gcaccagcag gcccaccagt tggagtaaaa gtgacattaa tagaggatga cactgccctg   1440

gtttcttgga aacccccctga tggcccagaa acagttgtga cccgctatac tatcttatat   1500

gcatctagga aggcctggat tgcaggagag tggcaggtct tacaccgtga aggggcaata   1560

accatggctt tgctagaaaa cttggtagca ggaaatgtgt acattgtcaa gatatctgca   1620

tccaatgagg tgggagaagg acccttttca aattctgtgg agctggcagt acttccaaag   1680

gaaacctctg aatcaaatca gaggcccaag cgtttagatt ctgctgatgc caaagtttat   1740

tcaggatatt accatctgga ccaaaaatca atgactggca ttgctgtagg tgttggcata   1800

gccttgacct gcatcctcat ctgtgttctc atcttgatat accgaagtaa agccaggaaa   1860

tcatctgctt ccaagacggc acagaatgga actcaacagt tacctcgtac cagtgcctcc   1920

ttagctagtg gaaatgaggt aggaaagaac ctggaaggag ctgtaggaaa tgaagaatct   1980

ttaatgccaa tgatcatgcc aaacagcttc attgatgcaa agggaggaac tgacctgata   2040

attaatagct atggtcctat aattaaaaac aactctaaga aaaagtggtt ttttttccaa   2100

gactcaaaga agatacaagt tgagcagcct caaagaagat ttactccagc ggtctgcttt   2160

taccagccag gcaccactgt attaatcagt gatgaagact cccctagctc cccaggtcag   2220

acaaccagct tctcaagacc ctttggtgtt gcagctgata cagaacattc agcaaatagt   2280

gaaggcagcc atgagactgg ggattctggg cggttttctc atgagtccaa cgatgagata   2340

catctgtcct cagttataag taccacaccc cccaacctct ga                       2382
```

<210> SEQ ID NO 28
<211> LENGTH: 793
<212> TYPE: PRT
<213> ORGANISM: homo sapiens

<400> SEQUENCE: 28

```
Met Ser Trp Leu Lys Asn Gly Arg Lys Ile His Ser Asn Gly Arg Ile
 1               5                  10                  15

Lys Met Tyr Asn Ser Lys Leu Val Ile Asn Gln Ile Ile Pro Glu Asp
            20                  25                  30

Asp Ala Ile Tyr Gln Cys Met Ala Glu Asn Ser Gln Gly Ser Ile Leu
        35                  40                  45
```

-continued

```
Ser Arg Ala Arg Leu Thr Val Val Met Ser Glu Asp Arg Pro Ser Ala
    50                  55                  60

Pro Tyr Asn Val His Ala Glu Thr Met Ser Ser Ser Ala Ile Leu Leu
65                  70                  75                  80

Ala Trp Glu Arg Pro Leu Tyr Asn Ser Asp Lys Val Ile Ala Tyr Ser
                85                  90                  95

Val His Tyr Met Lys Ala Glu Gly Leu Asn Asn Glu Glu Tyr Gln Val
            100                 105                 110

Val Ile Gly Asn Asp Thr Thr His Tyr Ile Ile Asp Asp Leu Glu Pro
        115                 120                 125

Ala Ser Asn Tyr Thr Phe Tyr Ile Val Ala Tyr Met Pro Met Gly Ala
    130                 135                 140

Ser Gln Met Ser Asp His Val Thr Gln Asn Thr Leu Glu Asp Val Pro
145                 150                 155                 160

Leu Arg Pro Pro Glu Ile Ser Leu Thr Ser Arg Ser Pro Thr Asp Ile
                165                 170                 175

Leu Ile Ser Trp Leu Pro Ile Pro Ala Lys Tyr Arg Arg Gly Gln Val
            180                 185                 190

Val Leu Tyr Arg Leu Ser Phe Arg Leu Ser Thr Glu Asn Ser Ile Gln
        195                 200                 205

Val Leu Glu Leu Pro Gly Thr Thr His Glu Tyr Leu Leu Glu Gly Leu
    210                 215                 220

Lys Pro Asp Ser Val Tyr Leu Val Arg Ile Thr Ala Ala Thr Arg Val
225                 230                 235                 240

Gly Leu Gly Glu Ser Ser Val Trp Thr Ser His Arg Thr Pro Lys Ala
                245                 250                 255

Thr Ser Val Lys Ala Pro Lys Ser Pro Glu Leu His Leu Glu Pro Leu
            260                 265                 270

Asn Cys Thr Thr Ile Ser Val Arg Trp Gln Gln Asp Val Glu Asp Thr
        275                 280                 285

Ala Ala Ile Gln Gly Tyr Lys Leu Tyr Tyr Lys Glu Glu Gly Gln Gln
    290                 295                 300

Glu Asn Gly Pro Ile Phe Leu Asp Thr Lys Asp Leu Leu Tyr Thr Leu
305                 310                 315                 320

Ser Gly Leu Asp Pro Arg Arg Lys Tyr His Val Arg Leu Leu Ala Tyr
                325                 330                 335

Asn Asn Ile Asp Asp Gly Tyr Gln Ala Asp Gln Thr Val Ser Thr Pro
            340                 345                 350

Gly Cys Val Ser Val Arg Asp Arg Met Val Pro Pro Pro Pro Pro Pro
        355                 360                 365

His His Leu Tyr Ala Lys Ala Asn Thr Ser Ser Ser Ile Phe Leu His
    370                 375                 380

Trp Arg Arg Pro Ala Phe Thr Ala Ala Gln Ile Ile Asn Tyr Thr Ile
385                 390                 395                 400

Arg Cys Asn Pro Val Gly Leu Gln Asn Ala Ser Leu Val Leu Tyr Leu
                405                 410                 415

Gln Thr Ser Glu Thr His Met Leu Val Gln Gly Leu Glu Pro Asn Thr
            420                 425                 430

Lys Tyr Glu Phe Ala Val Arg Leu His Val Asp Gln Leu Ser Ser Pro
        435                 440                 445

Trp Ser Pro Val Val Tyr His Ser Thr Leu Pro Glu Ala Pro Ala Gly
    450                 455                 460

Pro Pro Val Gly Val Lys Val Thr Leu Ile Glu Asp Asp Thr Ala Leu
```

-continued

```
465                 470                 475                 480

Val Ser Trp Lys Pro Pro Asp Gly Pro Glu Thr Val Val Thr Arg Tyr
                485                 490                 495

Thr Ile Leu Tyr Ala Ser Arg Lys Ala Trp Ile Ala Gly Glu Trp Gln
            500                 505                 510

Val Leu His Arg Glu Gly Ala Ile Thr Met Ala Leu Leu Glu Asn Leu
        515                 520                 525

Val Ala Gly Asn Val Tyr Ile Val Lys Ile Ser Ala Ser Asn Glu Val
    530                 535                 540

Gly Glu Gly Pro Phe Ser Asn Ser Val Glu Leu Ala Val Leu Pro Lys
545                 550                 555                 560

Glu Thr Ser Glu Ser Asn Gln Arg Pro Lys Arg Leu Asp Ser Ala Asp
                565                 570                 575

Ala Lys Val Tyr Ser Gly Tyr Tyr His Leu Asp Gln Lys Ser Met Thr
            580                 585                 590

Gly Ile Ala Val Gly Val Gly Ile Ala Leu Thr Cys Ile Leu Ile Cys
        595                 600                 605

Val Leu Ile Leu Ile Tyr Arg Ser Lys Ala Arg Lys Ser Ser Ala Ser
    610                 615                 620

Lys Thr Ala Gln Asn Gly Thr Gln Gln Leu Pro Arg Thr Ser Ala Ser
625                 630                 635                 640

Leu Ala Ser Gly Asn Glu Val Gly Lys Asn Leu Glu Gly Ala Val Gly
                645                 650                 655

Asn Glu Glu Ser Leu Met Pro Met Ile Met Pro Asn Ser Phe Ile Asp
            660                 665                 670

Ala Lys Gly Gly Thr Asp Leu Ile Ile Asn Ser Tyr Gly Pro Ile Ile
        675                 680                 685

Lys Asn Asn Ser Lys Lys Lys Trp Phe Phe Phe Gln Asp Ser Lys Lys
    690                 695                 700

Ile Gln Val Glu Gln Pro Gln Arg Arg Phe Thr Pro Ala Val Cys Phe
705                 710                 715                 720

Tyr Gln Pro Gly Thr Thr Val Leu Ile Ser Asp Glu Asp Ser Pro Ser
                725                 730                 735

Ser Pro Gly Gln Thr Thr Ser Phe Ser Arg Pro Phe Gly Val Ala Ala
            740                 745                 750

Asp Thr Glu His Ser Ala Asn Ser Glu Gly Ser His Glu Thr Gly Asp
        755                 760                 765

Ser Gly Arg Phe Ser His Glu Ser Asn Asp Glu Ile His Leu Ser Ser
    770                 775                 780

Val Ile Ser Thr Thr Pro Pro Asn Leu
785                 790
```

<210> SEQ ID NO 29
<211> LENGTH: 1887
<212> TYPE: DNA
<213> ORGANISM: homo sapiens

<400> SEQUENCE: 29

```
atgtcatggt tgaaaaatgg aaggaagata cattcgaatg gtagaattaa aatgtacaac     60

agtaaattgg taattaacca gattattcct gaagatgatg ctatttatca gtgcatggct    120

gagaatagcc aaggatctat tttatctaga gccagactga ctgtagtgat gtcagaagac    180

agacccagtg ctccctataa tgtacatgct gaaaccatgt caagctcagc cattctttta    240

gcctgggaga ggccacttta taattcagac aaagtcattg cctattctgt acactacatg    300
```

-continued

```
aaagcagaag gtttaaataa tgaagagtat caagtagtca tcggaaatga cacaactcat    360
tatattattg atgacttaga gcctgccagc aattatactt tctacattgt agcatatatg    420
ccaatgggag ccagccagat gtctgaccat gtgacacaga atactctaga ggatgacccc    480
agaagaaaat atcatgtgag actcctggct tacaacaaca tagacgatgg ctatcaggca    540
gatcagactg tcagcactcc aggatgcgtg tctgttcgtg atcgcatggt ccctcctcca    600
ccaccacccc accatctcta tgcgaaggct aacacctcat cttccatctt cctgcactgg    660
aggaggcctg cattcaccgc tgcacaaatc attaactaca ccatccgctg taatcctgtt    720
ggcctgcaga atgcttcttt ggttctgtac cttcaaacat cagaaactca catgttggtt    780
caaggtctag aaccaaacac caaatacgaa tttgccgttc gattacatgt ggatcagctt    840
tccagtcctt ggagccctgt agtctaccat tctactcttc cagaagcacc agcaggccca    900
ccagttggag taaaagtgac attaatagag gatgacactg ccctggtttc ttggaaaccc    960
cctgatggcc cagaaacagt tgtgacccgc tatactatct tatatgcatc taggaaggcc   1020
tggattgcag gagagtggca ggtcttacac cgtgaagggg caataaccat ggctttgcta   1080
gaaaacttgg tagcaggaaa tgtgtacatt gtcaagatat ctgcatccaa tgaggtggga   1140
gaaggaccct tttcaaattc tgtggagctg gcagtacttc caaaggaaac ctctgaatca   1200
aatcagaggc ccaagcgttt agattctgct gatgccaaag tttattcagg atattaccat   1260
ctggaccaaa aatcaatgac tggcattgct gtaggtgttg gcatagcctt gacctgcatc   1320
ctcatctgtg ttctcatctt gatataccga agtaaagcca ggaaatcatc tgcttccaag   1380
acggcacaga atggaactca acagttacct cgtaccagtg cctccttagc tagtggaaat   1440
gaggtaggaa agaacctgga aggagctgta ggaaatgaag aatctttaat gccaatgatc   1500
atgccaaaca gcttcattga tgcaaaggga ggaactgacc tgataattaa tagctatggt   1560
cctataatta aaaacaactc taagaaaaag tggtttttttt tccaagactc aaagaagata   1620
caagttgagc agcctcaaag aagatttact ccagcggtct gcttttacca gccaggcacc   1680
actgtattaa tcagtgatga agactcccct agctccccag gtcagacaac cagcttctca   1740
agaccctttg gtgttgcagc tgatacagaa cattcagcaa atagtgaagg cagccatgag   1800
actggggatt ctgggcggtt ttctcatgag tccaacgatg agatacatct gtcctcagtt   1860
ataagtacca caccccccaa cctctga                                        1887
```

```
<210> SEQ ID NO 30
<211> LENGTH: 628
<212> TYPE: PRT
<213> ORGANISM: homo sapiens

<400> SEQUENCE: 30

Met Ser Trp Leu Lys Asn Gly Arg Lys Ile His Ser Asn Gly Arg Ile
 1               5                  10                  15

Lys Met Tyr Asn Ser Lys Leu Val Ile Asn Gln Ile Ile Pro Glu Asp
            20                  25                  30

Asp Ala Ile Tyr Gln Cys Met Ala Glu Asn Ser Gln Gly Ser Ile Leu
        35                  40                  45

Ser Arg Ala Arg Leu Thr Val Val Met Ser Glu Asp Arg Pro Ser Ala
    50                  55                  60

Pro Tyr Asn Val His Ala Glu Thr Met Ser Ser Ser Ala Ile Leu Leu
65                  70                  75                  80

Ala Trp Glu Arg Pro Leu Tyr Asn Ser Asp Lys Val Ile Ala Tyr Ser
```

-continued

```
                85                  90                  95

Val His Tyr Met Lys Ala Glu Gly Leu Asn Asn Glu Glu Tyr Gln Val
            100                 105                 110

Val Ile Gly Asn Asp Thr Thr His Tyr Ile Ile Asp Asp Leu Glu Pro
        115                 120                 125

Ala Ser Asn Tyr Thr Phe Tyr Ile Val Ala Tyr Met Pro Met Gly Ala
    130                 135                 140

Ser Gln Met Ser Asp His Val Thr Gln Asn Thr Leu Glu Asp Asp Pro
145                 150                 155                 160

Arg Arg Lys Tyr His Val Arg Leu Leu Ala Tyr Asn Asn Ile Asp Asp
                165                 170                 175

Gly Tyr Gln Ala Asp Gln Thr Val Ser Thr Pro Gly Cys Val Ser Val
            180                 185                 190

Arg Asp Arg Met Val Pro Pro Pro Pro Pro Pro His His Leu Tyr Ala
        195                 200                 205

Lys Ala Asn Thr Ser Ser Ser Ile Phe Leu His Trp Arg Arg Pro Ala
    210                 215                 220

Phe Thr Ala Ala Gln Ile Ile Asn Tyr Thr Ile Arg Cys Asn Pro Val
225                 230                 235                 240

Gly Leu Gln Asn Ala Ser Leu Val Leu Tyr Leu Gln Thr Ser Glu Thr
                245                 250                 255

His Met Leu Val Gln Gly Leu Glu Pro Asn Thr Lys Tyr Glu Phe Ala
            260                 265                 270

Val Arg Leu His Val Asp Gln Leu Ser Ser Pro Trp Ser Pro Val Val
        275                 280                 285

Tyr His Ser Thr Leu Pro Glu Ala Pro Ala Gly Pro Pro Val Gly Val
    290                 295                 300

Lys Val Thr Leu Ile Glu Asp Asp Thr Ala Leu Val Ser Trp Lys Pro
305                 310                 315                 320

Pro Asp Gly Pro Glu Thr Val Val Thr Arg Tyr Thr Ile Leu Tyr Ala
                325                 330                 335

Ser Arg Lys Ala Trp Ile Ala Gly Glu Trp Gln Val Leu His Arg Glu
            340                 345                 350

Gly Ala Ile Thr Met Ala Leu Leu Glu Asn Leu Val Ala Gly Asn Val
        355                 360                 365

Tyr Ile Val Lys Ile Ser Ala Ser Asn Glu Val Gly Glu Gly Pro Phe
    370                 375                 380

Ser Asn Ser Val Glu Leu Ala Val Leu Pro Lys Glu Thr Ser Glu Ser
385                 390                 395                 400

Asn Gln Arg Pro Lys Arg Leu Asp Ser Ala Asp Ala Lys Val Tyr Ser
                405                 410                 415

Gly Tyr Tyr His Leu Asp Gln Lys Ser Met Thr Gly Ile Ala Val Gly
            420                 425                 430

Val Gly Ile Ala Leu Thr Cys Ile Leu Ile Cys Val Leu Ile Leu Ile
        435                 440                 445

Tyr Arg Ser Lys Ala Arg Lys Ser Ser Ala Ser Lys Thr Ala Gln Asn
    450                 455                 460

Gly Thr Gln Gln Leu Pro Arg Thr Ser Ala Ser Leu Ala Ser Gly Asn
465                 470                 475                 480

Glu Val Gly Lys Asn Leu Glu Gly Ala Val Gly Asn Glu Glu Ser Leu
                485                 490                 495

Met Pro Met Ile Met Pro Asn Ser Phe Ile Asp Ala Lys Gly Gly Thr
            500                 505                 510
```

-continued

```
Asp Leu Ile Ile Asn Ser Tyr Gly Pro Ile Ile Lys Asn Asn Ser Lys
        515                 520                 525

Lys Lys Trp Phe Phe Phe Gln Asp Ser Lys Lys Ile Gln Val Glu Gln
    530                 535                 540

Pro Gln Arg Arg Phe Thr Pro Ala Val Cys Phe Tyr Gln Pro Gly Thr
545                 550                 555                 560

Thr Val Leu Ile Ser Asp Glu Asp Ser Pro Ser Ser Pro Gly Gln Thr
                565                 570                 575

Thr Ser Phe Ser Arg Pro Phe Gly Val Ala Ala Asp Thr Glu His Ser
            580                 585                 590

Ala Asn Ser Glu Gly Ser His Glu Thr Gly Asp Ser Gly Arg Phe Ser
        595                 600                 605

His Glu Ser Asn Asp Glu Ile His Leu Ser Ser Val Ile Ser Thr Thr
    610                 615                 620

Pro Pro Asn Leu
625


<210> SEQ ID NO 31
<211> LENGTH: 3874
<212> TYPE: DNA
<213> ORGANISM: homo sapiens

<400> SEQUENCE: 31

tgcttctcgc gagcggccgt ccgagcacca gcctcgccgc cgcagagacg ctcgccacgc     60

cggtgccgga gccggagcgg ggagccaggc tgcgtgcgac cagccgcaga gcagagagcg    120

cccggggcgg gggccgcaga cggacagggg ctctgggcgg ccggggagca tgcccgcgcg    180

gctacgctga atggcgcctc ctctgcgacc cctcgcccgg ctgcgaccgc cggggatgct    240

gctccgcgcg ctcctgctcc tgctgmtgct cagtcctttg ccaggagtgt ggtgctttag    300

cgaactgtct tttgtaaaag aaccacagga tgtaactgtc acaagaaagg acccagtcgt    360

tttagattgc caggctcacg gagaagttcc tattaaggtc acatggttga aaaatggagc    420

aaaaatgtct gaaaataaac ggatcgaggt tctttctaac ggctctttat acatcagtga    480

ggtggaaggc aggcgaggag agcagtccga tgaaggattt tatcagtgct tggcaatgaa    540

caaatatgga gccattctta gtcaaaaagc tcatcttgcc ttatcaacta tttctgcatt    600

tgaagtccag ccaatttcca ctgaggtcca cgaaggtgga gttgctcgat ttgcatgcaa    660

gatttcatcc caccctcctg cagtcataac atgggagttc aatcggacaa ctctacctat    720

gactatggac aggataactg ccctaccaac aggagtattg cagatctatg atgtcagcca    780

aagggattct ggaaattatc gttgtattgc tgccactgta gcccaccgac gtaaaagtat    840

ggaggcctcg ctaactgtga ttccagctaa ggagtcaaaa tccttccaca caccarcaat    900

tatagcaggt ccacagaaca taacaacatc tcttcatcag actgtagttt tggaatgcat    960

ggccacagga aatcccaaac caatcatttc ttggagccgc cttgatcaca aatccattga   1020

tgtctttaat actcgggtac ttggaaatgg taatctcatg atatctgatg tcaggctaca   1080

acatgctgga gtatatgttt gtcgggccac taccccctggc acacgcaact ttacagttgc  1140

tatggcaact ttaactgtat tagctcctcc ttcatttgtt gaatggccag aaagtttaac   1200

aaggcctcga gctggcactg ctcgatttgt gtgtcaggca gaaggaatcc cctctcccaa   1260

gatgtcatgg ttgaaaaatg gaaggaagat acattcgaat ggtagaatta aaatgtacaa   1320

cagtaaattg gtaattaacc agattattcc tgaagatgat gctatttatc agtgcatggc   1380
```

-continued

```
tgagaatagc caaggatcta ttttatctag agccagactg actgtagtga tgtcagaaga   1440
cagacccagt gctccctata atgtacatgc tgaaaccatg tcaagctcag ccattctttt   1500
agcctgggag aggccacttt ataattcaga caaagtcatt gcctattctg tacactacat   1560
gaaagcagaa ggtttaaata atgaagagta tcaagtagtc atcggaaatg acacaactca   1620
ttatattatt gatgacttag agcctgccag caattatact ttctacattg tagcatatat   1680
gccaatggga gccagccaga tgtctgacca tgtgacacag aatactctag aggatgttcc   1740
cctgagacct cctgaaatta gtttgacaag tcgaagtccc actgatattc tcatctcctg   1800
gctgccaatc ccagccaaat atcggcgggg ccaagtggtg ctgtatcgct tgtctttccg   1860
cctaagtact gagaattcaa tccaagttct ggagctcccg gggaccacgc atgagtacct   1920
tttggaaggc ctgaaacctg acagtgtcta cctggttcgg attactgctg ccaccagagt   1980
ggggctggga gagtcatcag tatggacttc acataggacg cccaaagcta caagcgtgaa   2040
agcccctaag tctccagagt tgcatttgga gcctctgaac tgtaccacca tttctgtgag   2100
gtggcagcaa gatgtagagg acacagctgc tattcagggc tacaagctgt actacaagga   2160
agaagggcag caggagaatg ggcccatttt cttggatacc aaggacctac tctatactct   2220
cagtggctta gaccccagaa gaaaatatca tgtgagactc ctggcttaca acaacataga   2280
cgatggctat caggcagatc agactgtcag cactccagga tgcgtgtctg ttcgtgatcg   2340
catggtccct cctccaccac caccccacca tctctatgcg aaggctaaca cctcatcttc   2400
catcttcctg cactggagga ggcctgcatt caccgctgca caaatcatta actacaccat   2460
ccgctgtaat cctgttggcc tgcagaatgc ttctttggtt ctgtaccttc aaacatcaga   2520
aactcacatg ttggttcaag gtctagaacc aaacaccaaa tacgaatttg ccgttcgatt   2580
acatgtggat cagctttcca gtccttggag ccctgtagtc taccattcta ctcttccaga   2640
agcaccagca ggcccaccag ttggagtaaa agtgacatta atagaggatg acactgccct   2700
ggtttcttgg aaacccccctg atggcccaga aacagttgtg acccgctata ctatcttata   2760
tgcatctagg aaggcctgga ttgcaggaga gtggcaggtc ttacaccgtg aaggggcaat   2820
aaccatggct ttgctagaaa acttggtagc aggaaatgtg tacattgtca agatatctgc   2880
atccaatgag gtgggagaag gacccttttc aaattctgtg gagctggcag tacttccaaa   2940
ggaaacctct gaatcaaatc agaggcccaa gcgtttagat tctgctgatg ccaaagttta   3000
ttcaggatat taccatctgg accaaaaatc aatgactggc attgctgtag gtgttggcat   3060
agccttgacc tgcatcctca tctgtgttct catcttgata taccgaagta aagccaggaa   3120
atcatctgct tccaagacgg cacagaatgg aactcaacag ttacctcgta ccagtgcctc   3180
cttagctagt ggaaatgagg taggaaagaa cctggaagga gctgtaggaa atgaagaatc   3240
tttaatgcca atgatcatgc caaacagctt cattgatgca aagggaggaa ctgacctgat   3300
aattaatagc tatggtccta taattaaaaa caactctaag aaaaagtggt tttttttcca   3360
agactcaaag aagatacaag ttgagcagcc tcaaagaaga tttactccag cggtctgctt   3420
ttaccagcca ggcaccactg tattaatcag tgatgaagac tcccctagct ccccaggtca   3480
gacaaccagc ttctcaagac cctttggtgt tgcagctgat acagaacatt cagcaaatag   3540
tgaaggcagc catgagactg gggattctgg gcggttttct catgagtcca acgatgagat   3600
acatctgtcc tcagttataa gtaccacacc ccccaacctc tgattctttc actggcagtg   3660
attcaggtgg agattccgca ttgaggaagt gtgaagaccc tgctgtgtca tctgttagtg   3720
agcagacttc ctccttagtt ctgcagccgc catctgccat gctatgcttt gataaaaatg   3780
```

-continued

```
attttccaat ctagacggcc atgctcaggt attctcacca ttaaatctgt tcgaaggaca   3840

atgaacaggg aaccaaaaaa aaaaaaaaaa aaaa                               3874
```

HUMAN PHOSPHATASES AND POLYNUCLEOTIDES ENCODING THE SAME

The present application claims the benefit of U.S. Provisional Application No. 60/210,607 which was filed on Jun. 9, 2000 and is herein incorporated by reference in its entirety.

1. INTRODUCTION

The present invention relates to the discovery, identification, and characterization of novel human polynucleotides encoding proteins that share sequence similarity with animal phosphatases. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, the treatment of physiological disorders, or otherwise contributing to the quality of life.

2. BACKGROUND OF THE INVENTION

Membrane proteins can act as, inter alia, ligand receptors, signal transducers, neuronal guidance proteins, cell adhesion proteins, cell surface markers, and can also possess enzymatic functions such as the phosphorylation of substrates (i.e., kinase activity). Phosphatases mediate dephosphorylation of a wide variety of proteins and compounds in the cell. Often working in conjunction with kinases, phosphatases are involved in a regulating a wide range of biochemical and physiological pathways. Given the physiological importance of phosphatases, they have been subject to significant scrutiny and are good drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal immunoglobulin super family cell surface proteins, proteins that play a role in neuronal guidance (e.g., nope, punc, unc, and neogenin), phosphatases, netrin receptors, DCC (deleted in colon cancer) including, but not limited to tyrosine phosphatases, and cell adhesion molecules as homologues and orthologs across a range of phyla and species.

The novel human polynucleotides described herein, encode open reading frames (ORFs) encoding proteins of 1,069, 380, 904, 1150, 985, 991, 302, 826, 1072, 907, 712, 624, 547, 793, and 628 amino acids in length (see SEQ ID NOS: 2, 4, 6, 8, 10, 12, 14, 16, 18, 20, 22, 24, 26, 28, and 30 respectively).

The invention also encompasses agonists and antagonists of the described NHPs, including small molecules, large molecules, mutant NHPS, or portions thereof that compete with native NHPs, NHP peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described gene under the control of a strong promoter system). The present invention also includes both transgenic animals that express a NHP transgene, and NHP "knock-outs" (which can be conditional) that do not express a functional NHP. Knockout murine ES cells have been produced in a murine ortholog of the described NHPs.

Further, the present invention also relates to processes for identifying compounds that modulate, i.e., act as agonists or antagonists, of NHP expression and/or NHP product activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human phosphatase proteins. SEQ ID NO:31 describes a NHP ORF and flanking sequences.

5. DETAILED DESCRIPTION OF THE INVENTION

The NHPs, described for the first time herein, are novel proteins that are expressed in, inter alia, human cell lines, and human brain, pituitary, kidney, testis, thyroid, adrenal gland, stomach, heart, uterus, placenta, mammary gland, adipose, esophagus, cervix, rectum, pericardium, ovary, fetal kidney and gene trapped human cells. The described sequences were compiled from gene trapped sequences in conjunction with sequences available in GENBANK, and cDNAs isolated from human testis and thyroid cDNA libraries (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of an NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. Nos. 5,723,323 and 5,837,458 both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of a sequence presented in the Sequence Listing (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format), Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled NHP fusion proteins, such as, for example, AP-NHP or NHP-AP fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, regulatable, viral (particularly retroviral LTR promoters) the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic proteins, expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequences and corresponding deduced amino acid sequences of the described NHPs are presented in the Sequence Listing. The NHP nucleotide sequences were obtained using the sequence information present in human gene trapped sequence tags and other cDNA sequences. Expression analysis has provided evidence that the described NHPs can be expressed in a wide variety of human tissues as well as gene trapped human cells. In addition to tyrosine phosphatases, the described NHPs also share significant similarity to a range of additional Ig super family proteins from a range of phyla and species. Given the physiological importance of protein phosphatases and other proteins that display structural relatedness to the described NHPs, such proteins have been subject to intense scrutiny as exemplified and discussed in U.S. Pat. Nos. 5,939,271 and 6,020,179 which describe a variety of uses and applications that can be applied to the described NHP sequences and which are herein incorporated by reference in their entirety.

Several polymorphisms were identified during sequencing such as an A-C transversion that can occur in the sequence region represented by, for example, nucleotide position 76 of SEQ ID NO:1 which can result in a L or M being present in the corresponding amino acid sequence at position, for example, 26 of SEQ ID NO:2, and an A-G transition that can occur in the sequence region represented by, for example, nucleotide position 706 of SEQ ID NO:1 which can result in a T or A being present in the corresponding amino acid sequence at, for example, position 236 of SEQ ID NO:2. The present invention contemplates sequences incorporating any of the above polymorphisms as well as all combinations and permutations thereof.

The gene encoding the described NHPs is apparently present on human chromosome 15 or human chromosome 3 (see GENBANK accession nos. AC012378 and AC012674). Accordingly, the described sequences are useful for identifying and mapping the coding regions of the human genome as well as identifying biologically validating functional exon splice junctions.

5.2 NHPS AND NHP POLYPEPTIDES

The described NHP products, polypeptides, peptide fragments, mutated, truncated, or deleted forms of the NHPs, and/or NHP fusion proteins can be prepared for a variety of uses, including but not limited to the generation of antibodies, as reagents in diagnostic assays (e.g., for cancer, neuronal abnormalities, Barbet-Biel Syndrome, etc.), the identification of other cellular gene products related to the NHP, as reagents in assays for screening for compounds that can be used as pharmaceutical reagents useful in the therapeutic treatment of mental, biological, or medical disorders and disease.

The Sequence Listing discloses the amino acid sequence encoded by the described NHP-encoding polynucleotides. The NHPs have initiator methionines in DNA sequence contexts consistent with eucaryotic translation initiation site, and display an apparent signal sequence near the N-terminus which indicates that the NHPs can be membrane associated, secreted, or cytoplasmic.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by a NHP nucleotide sequence described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP encoding polynucleotide sequence can be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems can be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544– 546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence that:

(a) encodes the amino acid sequence shown in SEQ ID NO:8; and (b) hybridizes under stringent conditions to the nucleotide sequence of SEQ ID NO:7 or the complement thereof.

2. An isolated nucleic acid molecule comprising a nucleotide sequence encoding the amino acid sequence shown in SEQ ID NO:8.

* * * * *